United States Patent
Briere et al.

(10) Patent No.: US 12,269,857 B2
(45) Date of Patent: *Apr. 8, 2025

(54) PROTEIN TYROSINE-TYROSINE ANALOGS AND METHODS OF USING THE SAME

(71) Applicant: Eli Lilly and Company, Indianapolis, IN (US)

(72) Inventors: Daniel Anthony Briere, Morgantown, IN (US); Daniel Christopher Lopes, Zionsville, IN (US); Avinash Muppidi, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/484,451

(22) Filed: Oct. 11, 2023

(65) Prior Publication Data

US 2024/0209055 A1 Jun. 27, 2024

Related U.S. Application Data

(63) Continuation of application No. 17/494,394, filed on Oct. 5, 2021, now Pat. No. 11,820,803, which is a continuation of application No. 16/665,072, filed on Oct. 28, 2019, now Pat. No. 11,155,592.

(60) Provisional application No. 62/793,544, filed on Jan. 17, 2019, provisional application No. 62/754,244, filed on Nov. 1, 2018.

(51) Int. Cl.
| | |
|---|---|
| A61K 38/00 | (2006.01) |
| A61P 3/04 | (2006.01) |
| C07K 14/575 | (2006.01) |
| A61K 9/00 | (2006.01) |
| A61K 45/06 | (2006.01) |

(52) U.S. Cl.
CPC .......... *C07K 14/57545* (2013.01); *A61P 3/04* (2018.01); *A61K 9/0053* (2013.01); *A61K 38/00* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 11,155,592 B2 * | 10/2021 | Briere | .................. | C07K 14/575 |
| 11,820,803 B2 * | 11/2023 | Briere | .............. | C07K 14/57545 |

FOREIGN PATENT DOCUMENTS

| | | |
|---|---|---|
| EP | 2329839 B1 | 1/2003 |
| WO | 2002047712 A2 | 6/2002 |
| WO | 2009/138511 | 11/2009 |
| WO | 2011033068 A1 | 3/2011 |
| WO | 2011/058165 A1 | 5/2011 |
| WO | 2014178018 A1 | 11/2014 |
| WO | 2015071355 A1 | 5/2015 |
| WO | 2004089279 A2 | 10/2016 |
| WO | 2016198682 A1 | 12/2016 |

OTHER PUBLICATIONS

Ortiz, A. A., Milardo, L. F., DeCarr, L. B., Buckholz, T. M., Mays, M. R., Claus, T. H., . . . & Lumb, K. J. (2007). A novel long-acting selective neuropeptide Y2 receptor polyethylene glycol-conjugated peptide agonist reduces food intake and body weight and improves glucose metabolism in rodents. *Journal of Pharmacology and Experimental Therapeutics*, 323(2), 692-700.

DeCarr, L. B., Buckholz, T. M., Milardo, L. F., Mays, M. R., Ortiz, A., & Lumb, K. J. (2007). A long-acting selective neuropeptide Y2 receptor PEGylated peptide agonist reduces food intake in mice. *Bioorganic & medicinal chemistry letters*, 17(7), 1916-1919.

Patent Cooperation Treaty International Search Report and Written Opinion of the International Searching Authority pertaining to International Application No. PCT /US2019/058259; International Filing Date: Oct. 28, 2019; Date of Mailing: Mar. 11, 2020.

* cited by examiner

*Primary Examiner* — Aradhana Sasan
*Assistant Examiner* — Mercy H Sabila
(74) *Attorney, Agent, or Firm* — Charles H. Rexer

(57) ABSTRACT

PYY analogs are disclosed that include modifications that increase half-life when compared to native, human PYY, as well as additional modifications that increase potency and selectivity to the NPY2 receptor. Pharmaceutical compositions also are disclosed that include one or more of the PYY analogs described herein in a pharmaceutically acceptable carrier. Methods of making and using the PYY analogs also are disclosed, especially for treating obesity and obesity-related diseases and disorders such as type II diabetes mellitus.

12 Claims, No Drawings

Specification includes a Sequence Listing.

```
                          SEQUENCE LISTING

Sequence total quantity: 15
SEQ ID NO: 1            moltype = AA  length = 36
FEATURE                 Location/Qualifiers
source                  1..36
                        mol_type = protein
                        organism = Homo sapiens
SEQUENCE: 1
YPIKPEAPGE DASPEELNRY YASLRHYLNL VTRQRY                                36

SEQ ID NO: 2            moltype = AA  length = 34
FEATURE                 Location/Qualifiers
source                  1..34
                        mol_type = protein
                        organism = Homo sapiens
SEQUENCE: 2
IKPEAPGEDA SPEELNRYYA SLRHYLNLVT RQRY                                  34

SEQ ID NO: 3            moltype = AA  length = 34
FEATURE                 Location/Qualifiers
source                  1..34
```

```
                    mol_type = protein
                    organism = synthetic construct
VARIANT             5
                    note = X at position 5 is any amino acid with a functional
                     group available for conjugation and the functional group
                     is conjugated to a C16-C22 fatty acid
VARIANT             7
                    note = X at position 7 is Glutamic Acid or Glycine
VARIANT             8
                    note = X at position 8 is Glutamic Acid or Lysine
VARIANT             15
                    note = X at position 15 is Leucine orTryptophan
VARIANT             16
                    note = X at position 16 is Asparagine or Glutamine
VARIANT             20
                    note = X at position 20 is Alanine or Isoleucine
VARIANT             21
                    note = X at position 21 is Glutamic Acid, Aspartic Acid, or
                     Serine
VARIANT             28
                    note = X at position 28 is Glutamic Acid orTryptophan
MOD_RES             34
                    note = position 34 C-terminal amino acid is optionally
                     amidated
SEQUENCE: 3
PKPEXPXXDA SPEEXXRYYX XLRHYLNXLT RQRY                                      34

SEQ ID NO: 4        moltype = AA   length = 34
FEATURE             Location/Qualifiers
source              1..34
                    mol_type = protein
                    organism = synthetic construct
SEQUENCE: 4
PKPEKPGEDA SPEEWQRYYA ELRHYLNWLT RQRY                                      34

SEQ ID NO: 5        moltype = AA   length = 34
FEATURE             Location/Qualifiers
source              1..34
                    mol_type = protein
                    organism = synthetic construct
SEQUENCE: 5
PKPEKPGEDA SPEEWQRYYA ELRHYLNELT RQRY                                      34

SEQ ID NO: 6        moltype = AA   length = 34
FEATURE             Location/Qualifiers
source              1..34
                    mol_type = protein
                    organism = synthetic construct
SEQUENCE: 6
PKPEKPEEDA SPEEWQRYYI ELRHYLNWLT RQRY                                      34

SEQ ID NO: 7        moltype = AA   length = 34
FEATURE             Location/Qualifiers
source              1..34
                    mol_type = protein
                    organism = synthetic construct
SEQUENCE: 7
PKPEKPGKDA SPEEWNRYYA DLRHYLNWLT RQRY                                      34

SEQ ID NO: 8        moltype = AA   length = 34
FEATURE             Location/Qualifiers
source              1..34
                    mol_type = protein
                    organism = synthetic construct
SEQUENCE: 8
PKPEKPGEDA SPEELQRYYA SLRHYLNWLT RQRY                                      34

SEQ ID NO: 9        moltype = AA   length = 34
FEATURE             Location/Qualifiers
source              1..34
                    mol_type = protein
                    organism = synthetic construct
MOD_RES             5
                    note = Lysine at position 5 is chemically modified by
                     conjugation of the epsilon-amino group of the Lysine side
                     chain with Aminohexanoic Acid-Glutamic Acid-Gamma Glutamic
                     Acid-CO-(CH2)16-CO2H
MOD_RES             34
                    note = Amidation
```

```
SEQUENCE: 9
PKPEKPGEDA SPEEWQRYYA ELRHYLNWLT RQRY                                              34

SEQ ID NO: 10              moltype = AA  length = 34
FEATURE                    Location/Qualifiers
source                     1..34
                           mol_type = protein
                           organism = synthetic construct
MOD_RES                    5
                           note = Lysine at position 5 is chemically modified by
                            conjugation of the epsilon-amino group of the Lysine side
                            chain with ([2-(2-amino-ethoxy)-ethoxy)]-acetic
                            acid)2-Gamma Glutamic Acid-CO-(CH2)18-CO2H
MOD_RES                    34
                           note = Amidation
SEQUENCE: 10
PKPEKPGEDA SPEEWQRYYA ELRHYLNELT RQRY                                              34

SEQ ID NO: 11              moltype = AA  length = 34
FEATURE                    Location/Qualifiers
source                     1..34
                           mol_type = protein
                           organism = synthetic construct
MOD_RES                    5
                           note = Lysine at position 5 is chemically modified by
                            conjugation of the epsilon-amino group of the Lysine side
                            chain with [[2-(2-amino-ethoxy)-ethoxy)]-acetic
                            acid]-Gamma Glutamic Acid-CO-(CH2)16-CO2H
MOD_RES                    34
                           note = Amidation
SEQUENCE: 11
PKPEKPEEDA SPEEWQRYYI ELRHYLNWLT RQRY                                              34

SEQ ID NO: 12              moltype = AA  length = 34
FEATURE                    Location/Qualifiers
source                     1..34
                           mol_type = protein
                           organism = synthetic construct
MOD_RES                    5
                           note = Lysine at position 5 is chemically modified by
                            conjugation of the epsilon-amino group of the Lysine side
                            chain with ([2-(2-amino-ethoxy)-ethoxy)]-acetic
                            acid)2-gamma glutamic acid-CO-(CH2)16-CO2H
MOD_RES                    34
                           note = Amidation
SEQUENCE: 12
PKPEKPGKDA SPEEWNRYYA DLRHYLNWLT RQRY                                              34

SEQ ID NO: 13              moltype = AA  length = 34
FEATURE                    Location/Qualifiers
source                     1..34
                           mol_type = protein
                           organism = synthetic construct
MOD_RES                    5
                           note = Lysine at position 5 is chemically modified by
                            conjugation of the epsilon-amino group of the Lysine side
                            chain with ([2-(2-amino-ethoxy)-ethoxy)]-acetic
                            acid)2-(gamma glutamic acid)3-CO-C18-CO2H
MOD_RES                    34
                           note = Amidation
SEQUENCE: 13
PKPEKPGEDA SPEELQRYYA SLRHYLNWLT RQRY                                              34

SEQ ID NO: 14              moltype = AA  length = 36
FEATURE                    Location/Qualifiers
source                     1..36
                           mol_type = protein
                           organism = Homo sapiens
```

```
SEQUENCE: 14
APLEPVYPGD NATPEQMAQY AADLRRYINM LTRPRY                              36

SEQ ID NO: 15           moltype = AA  length = 274
FEATURE                 Location/Qualifiers
source                  1..274
                        mol_type = protein
                        organism = Homo sapiens
SEQUENCE: 15
HGEGTFTSDV SSYLEEQAAK EFIAWLVKGR GGGGGSGGGG SGGGGSESKY GPPCPPCPAP    60
EAAGGPSVFL FPPKPKDTLM ISRTPEVTCV VVDVSQEDPE VQFNWYVDGV EVHNAKTKPR   120
EEQFNSTYRV VSVLTVLHQD WLNGKEYKCK VSNKGLPSSI EKTISKAKGQ PREPQVYTLP   180
PSQEEMTKNQ VSLTCLVKGF YPSDIAVEWE SNGQPENNYK TTPPVLDSDG SFFLYSRLTV   240
DKSRWQEGNV FSCSVMHEAL HNHYTQKSLS LSLG                               274
```

PROTEIN TYROSINE-TYROSINE ANALOGS AND METHODS OF USING THE SAME

CROSS REFERENCE TO RELATED APPLICATIONS

The application claims priority to U.S. Non-Provisional application Ser. No. 17/494,394, filed Oct. 5, 2021, which is a continuation of U.S. Non-Provisional application Ser. No. 16/665,072, filed Oct. 28, 2019, which claims priority to U.S. Provisional Ser. No. 62/793,544, filed Jan. 17, 2019, and U.S. Provisional Ser. No. 62/754,244, filed Nov. 1, 2018, the contents of which are herein incorporated by reference in their entirety.

REFERENCE TO SEQUENCE LISTING SUBMITTED ELECTRONICALLY

The disclosure is being filed along with a Sequence Listing in ST.26 XML format. The Sequence Listing is provided as a file title "X21917B_US_Sequence_Listing_20240319" created on Mar. 19, 2024 and is 22.3 KB in size. The Sequence Listing information in the ST.26 XML format is incorporated herein by reference in its entirety.

The disclosure relates generally to biology and medicine, and more particularly it relates to Peptide Tyrosine-Tyrosine (PYY) analogs that can bind a neuropeptide Y (NPY) receptor such as the NPY2 receptor, as well as compositions including the same and their therapeutic use in treating obesity and obesity-related diseases and disorders such as type II diabetes (T2DM).

PYY is a member of the pancreatic polypeptide (PP) family and is involved in modulating food intake and energy expenditure following a meal (see, Tatemoto (1982) *Proc. Natl. Acad. Sci.* 79:2514-2518). PYY is secreted by L cells of the gastrointestinal track and has two main endogenous forms—$PYY_{1-36}$ (SEQ ID NO: 1) and $PYY_{3-36}$ (SEQ ID NO:2). $PYY_{1-36}$ predominates over $PYY_{3-36}$ during fasting, whereas $PYY_{3-36}$ predominates over $PYY_{1-36}$ following feeding. Dipeptidyl peptidase-IV (DPP-IV) hydrolyzes $PYY_{1-36}$ at a $Pro^2$-$Ile^3$ bond to produce $PYY_{3-36}$, which is more selective for the NPY2 receptor than $PYY_{1-36}$.

Plasma $PYY_{3-36}$ concentration typically increases within 15 minutes of food intake, peaks within 60-90 minutes, and remains elevated for up to 6 hours before returning to baseline (see, Adrian et al. (1985) *Gastroenterology* 89:1070-1077; and De Silva & Bloom (2012) *Gut Liver* 6:10-20). In this manner, $PYY_{3-36}$ is believed to impact appetite via its direct central effect and also via its effect on gut motility (i.e., its anorectic effect). Additionally, $PYY_{3-36}$ is believed to mediate insulin sensitivity to thereby help lower blood glucose (i.e., its sensitization effect).

$PYY_{3-36}$ has been investigated as a potential therapeutic agent for body-weight regulation in view of its anorectic effects, especially for treating obesity and its associated diseases and disorders, including T2DM and cardiovascular diseases (see, e.g., Intl. Patent Application Publication No. 2002/47712; and Schwartz & Morton (2002) *Nature* 418: 595-597).

Unfortunately, exogenously administered $PYY_{3-36}$ has a short half-life (e.g., about 10-15 minutes) due to proteases and other clearance mechanisms (see, Lluis et al. (1989) *Rev. Esp. Fisiol.* 45:377-384; and Torang et al. (2016) *Am. J. Physiol. Regul. Integr. Comp. Physiol.* 310:R866-R874), which presents challenges when using it as a therapeutic agent. With such a short half-life, $PYY_{3-36}$ should be administered at least once-daily to exert a therapeutic effect, which is inconvenient for an individual in need thereof. Efforts therefore have been made to increase $PYY_{3-36}$'s half-life and/or to increase its NPY2 receptor selectivity. For example, Rubinstein et al. describe PYY analogs having a 9-fluorenylmethoxy-carbonyl (Fmoc) or a 2-sulfo-9-fluorenyl-methoxycarbonyl (FMS) radical to increase half-life (see, Intl. Patent Application Publication No. WO 2004/089279). Moreover, DeCarr et al. describe PYY analogs having amino-terminally linked PEG moieties to increase half-life (see, DeCarr et al. (2007) *Bioorg. Med. Chem. Lett.* 17:1916-1919; see also, Ortiz et al. (2007) *J. Pharmacol. Exp. Ther.* 323:692-700). Furthermore, Kofoed et al. describe PYY analogs having albumin-binding side chains, at least one modified residue close to PYY's cleavage site (e.g. an N-methyl amino acid analog of an amino acid residue of interest), a N-glycine, and/or an arginine mimetic to increase half-life (see, Intl. Patent Application Publication No. WO 2011/033068).

Despite significant increases in understanding $PYY_{3-36}$'s role in metabolism, there remains a need for additional PYY analogs, especially PYY analogs having improved potency and selectivity at the NPY2 receptor.

As noted above, additional PYY analogs for therapeutic uses are needed. To address this need, the disclosure first describes PYY analogs that include a base amino acid sequence of (with respect to the numbering of native, human $PYY_{1-36}$ (SEQ ID NO:1)): $^3PKPEX_7PX_9X_{10}DASPEEX_{17}X_{18}RYYX_{22}X_{23}LRHYLNX_{30}LTRQRY^{36}$ (Formula I), where $X_7$ is any amino acid with a functional group available for conjugation and the functional group is conjugated to a $C_{16}$-$C_{22}$ fatty acid, $X_9$ is E or G, $X_{10}$ is E or K, $X_{17}$ is L or W, $X_{18}$ is N or Q, $X_{22}$ is A or I, $X_{23}$ is E, D or S, and $X_{30}$ is E or W (SEQ ID NO:3), and where a carboxy-terminal (C-terminal) amino acid optionally is amidated.

In certain instances, the amino acid with the functional group available for conjugation at position $X_7$ can be C, D, E, K or Q. In particular instances, the amino acid with the functional group available for conjugation at position $X_7$ is K, and the amino acid sequence can be one of the following:

```
                                            (SEQ ID NO: 4)
³PKPEKPGEDASPEEWQRYYAELRHYLNWLTRQRY³⁶, (SEQ ID NO: 5)
³PKPEKPGEDASPEEWQRYYAELRHYLNELTRQRY³⁶, (SEQ ID NO: 6)
³PKPEKPEEDASPEEWQRYYIELRHYLNWLTRQRY³⁶, (SEQ ID NO: 7)
³PKPEKPGKDASPEEWNRYYADLRHYLNWLTRQRY³⁶, or (SEQ ID NO: 8)
³PKPEKPGEDASPEELQRYYASLRHYLNWLTRQRY³⁶.
```

In some instances, the $C_{16}$-$C_{22}$ fatty acid is conjugated to the amino acid with the functional group available for conjugation via a linker. In certain instances, the $C_{16}$-$C_{22}$ fatty acid has a structure of —CO—$(CH_2)_a$—$CO_2H$, where a is an integer between 16 to 22. In particular instances, the fatty acid is a $C_{18}$ diacid or a $C_{20}$ diacid such as palmitic acid, stearic acid, arachidic acid or eicosanoic acid, especially a saturated $C_{18}$ diacid or $C_{20}$ diacid. Likewise, and in some instances, the linker can be one or more units of [2-(2-amino-ethoxy)-ethoxy)]-acetic acid (AEEA), aminohexanoic acid (Ahx), glutamic acid (E), γ-glutamic acid (γE) or combinations thereof.

In particular instances, the PYY analog can be one of the following:

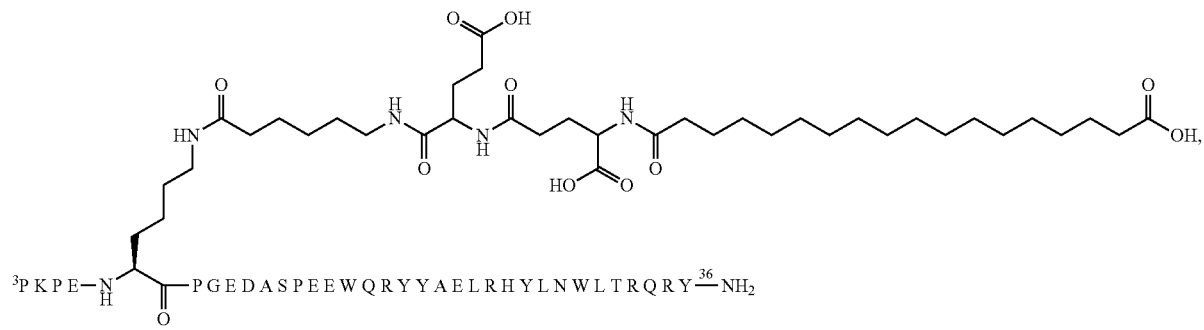
(SEQ ID NO:9)
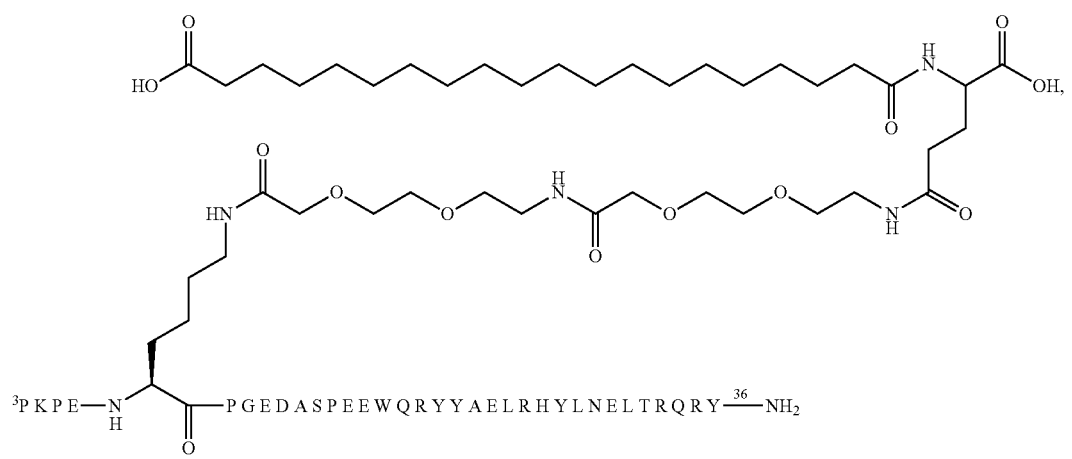
(SEQ ID NO:10)
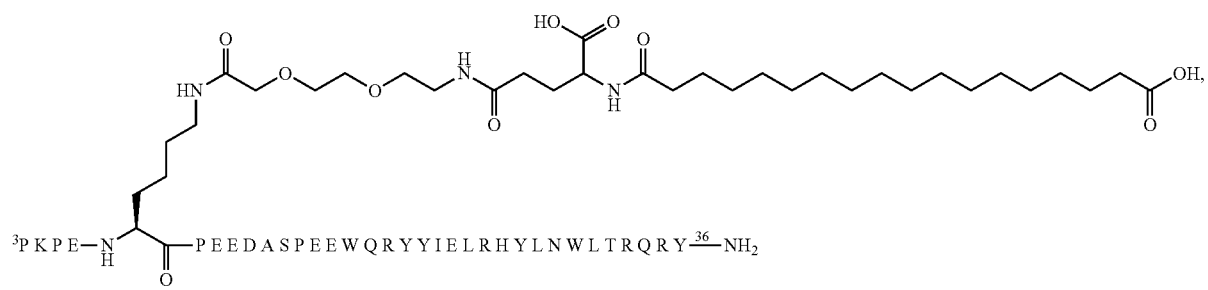
(SEQ ID NO:11)
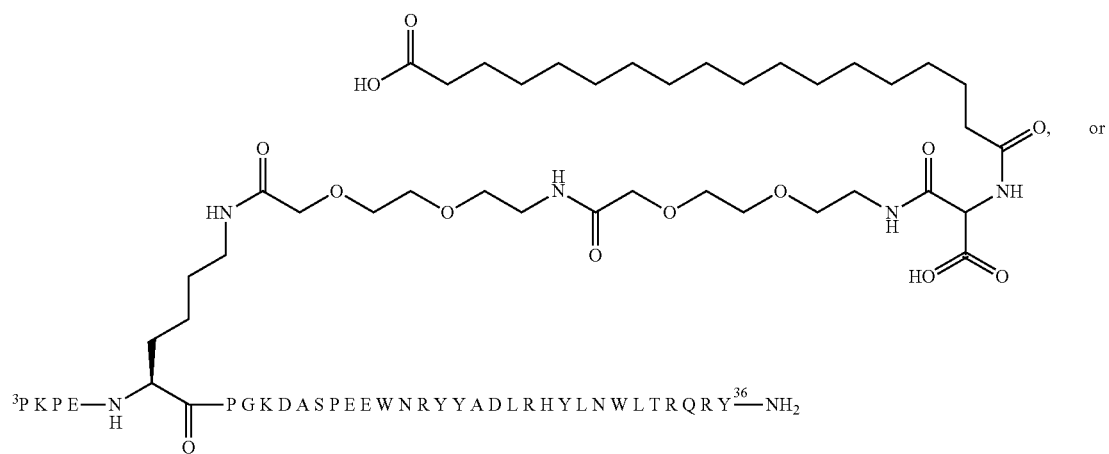
(SEQ ID NO:12)

(SEQ ID NO:13)

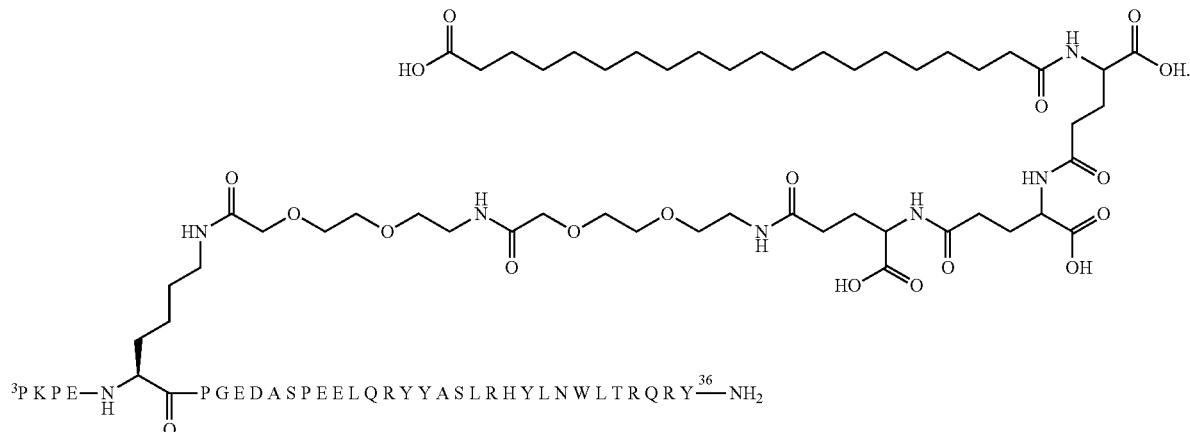

In some instances, the base structure of the PYY analogs herein further can include the two amino-terminal (N-terminal) amino acids of native, human PYY$_{1-36}$ (SEQ ID NO:1), which subsequently can be processed in vivo to a PYY$_{3-36}$ analog (i.e., the N-terminal "YP" residues of SEQ ID NO: 1 can be cleaved in vivo from any one of the PYY analogs).

In some instances, the PYY analogs have a charge of greater than −2, especially −3 or −4.

In some instances, the PYY analogs have a binding affinity at the human NPY2 receptor that is greater than that of human PYY$_{3-36}$ (SEQ ID NO:2), such as from about 2-fold greater to about 10-fold greater, especially about 2-fold greater to about 3-fold greater.

In some instances, the PYY analogs have a half-life that is longer than that of human PYY$_{3-36}$ (SEQ ID NO:2), such as from about 5 hours to about 24 hours longer, especially about 12 hours.

Second, pharmaceutical compositions are described that include at least one PYY analog herein or a pharmaceutically acceptable salt thereof (e.g., trifluroacetate salts, acetate salts or hydrochloride salts) and a pharmaceutically acceptable carrier. In some instances, the pharmaceutical compositions further can include carriers, diluents and/or excipients.

Moreover, the pharmaceutical compositions can include an additional therapeutic agent such as, for example, other antidiabetic or weight loss agents, especially an incretin. In some instances, the incretin can be glucagon (GCG) or a GCG analog. In other instances, the incretin can be glucagon-like peptide-1 (GLP-1), GLP-1 (7-36)$_{amide}$ or a GLP-1 analog. In other instances, the incretin can be gastric inhibitory peptide (GIP) or a GIP analog. In other instances, the incretin can be a dual receptor agonist such as oxyntomodulin (OXM) or an OXM analog, GLP-1/GCG or GIP/GLP-1. In other instances, the incretin can be an incretin analog having triple receptor activity (i.e., incretin analogs with activity at each of the GIP, GLP-1 and GCG receptors). In other instances, the additional therapeutic agent can be a DPP-IV inhibitor.

Third, methods are described for using the PYY analogs herein, especially for using the PYY analogs to treat obesity and obesity-related diseases and disorders such as T2DM. The methods include at least a step of administering to an individual in need thereof an effective amount of a PYY analog as described herein or a pharmaceutically acceptable salt thereof.

In some instances, the PYY analog can be subcutaneously (SQ) administered to the individual. Likewise, and in some instances, the PYY analog can be administered daily, every other day, three times a week, two times a week, one time a week (i.e., weekly), biweekly (i.e., every other week), or monthly. In certain instances, the PYY analog can be administered SQ every other day, SQ three times a week, SQ two times a week, SQ one time a week, SQ every other week, or SQ once a month. In particular instances, the PYY analog is administered SQ one time a week (QW).

Alternatively, the PYY analog can be orally administered to the individual. As above, the PYY analog can be administered daily, every other day, three times a week, two times a week, one time a week (i.e., weekly), biweekly (i.e., every other week), or monthly. In certain instances, the PYY analog can be administered orally every other day, orally three times a week, orally two times a week, orally one time a week, orally every other week, or orally once a month. In particular instances, the PYY analog is administered orally one time a week.

The methods also can include administering the at least one PYY analog in combination with an effective amount of an additional therapeutic agent such as a DPP-IV inhibitor or an incretin (e.g., GCG or a GCG analog, GLP-1, GLP-1 (7-36)$_{amide}$ or a GLP-1 analog, GIP or a GIP analog, OXM or an OXM analog, GIP/GLP-1, GLP-1/GCG, or an incretin having triple receptor activity). The DPP-IV inhibitor or incretin can be administered simultaneously, separately or sequentially with the PYY analog.

In some instances, the DPP-IV inhibitor or incretin can be administered with a frequency same as the PYY analog (i.e., every other day, twice a week, or even weekly). In other instances, the DPP-IV inhibitor or incretin is administered with a frequency distinct from the PYY analog. In other instances, the DPP-IV inhibitor or incretin is administered QW. In still other instances, the PYY analog is administered SQ, and the DPP-IV inhibitor or the incretin can be administered orally.

In some instances, the individual is obese or overweight. In other instances, the individual is a person with diabetes (PwD), especially T2DM. In certain instances, the individual is obese with T2DM or overweight with T2DM.

The methods also may include steps such as measuring or obtaining the individual's weight and/or blood glucose and/or hemoglobin A1c (HbA1c) and comparing such obtained values to one or more baseline values or previously obtained values to assess the effectiveness of treatment.

The methods also may be combined with diet and exercise and/or may be combined with additional therapeutic agents other than those discussed above.

Fourth, uses are described for the PYY analogs herein in treating obesity and obesity-related diseases and disorders such as T2DM, which optionally can be administered simultaneously, separately or sequentially (i.e., in combination) with a DPP-IV inhibitor and/or an incretin such as GCG or a GCG analog, GLP-1, GLP-1 (7-36)$_{amide}$ or a GLP-1 analog, GIP or a GIP analog, OXM or an OXM analog, GIP/GLP-1, GLP-1/GCG, or even an incretin having triple receptor activity.

Fifth, uses are described for the PYY analogs herein in manufacturing a medicament for treating obesity and obesity-related diseases and disorders such as T2DM, where the medicament optionally may further include a DPP-IV inhibitor and/or an incretin such as GCG or a GCG analog, GLP-1, GLP-1 (7-36)$_{amide}$ or a GLP-1 analog, GIP or a GIP analog, OXM or an OXM analog, GIP/GLP-1, GLP-1/GCG, or even an incretin having triple receptor activity.

One advantage of the PYY analogs herein is that they not only can facilitate weight loss but also can lower glucose. In this manner, individuals, especially those susceptible to or having T2DM, can delay progressing to exogenous insulin and can maintain target HbA1c goals. Moreover, the PYY analogs herein can enhance glycemic control by improving insulin sensitization. Combined, GIP/GLP-1 and PYY analog can be used for both glucose control (incretin+potential insulin sensitizer) and weight loss (synergistic). In particular, the PYY analogs herein can cause an up to about 12% weight loss alone when administered to an individual in need thereof and can cause an up to about 25% weight loss in connection with an additional therapeutic agent such as an incretin when administered to an individual in need thereof.

Another advantage of the PYY analogs herein is that they can have a half-life of up to about 24 hours, thereby allowing for once weekly administration.

Another advantage of the PYY analogs herein is that they have increased physico-chemical stability and compatibility when compared to native, human PYY$_{3-36}$ (SEQ ID NO:2) and increased compatibility in a formulation with incretins when compared to native, human PYY$_{3-36}$ (SEQ ID NO:2).

Unless defined otherwise, all technical and scientific terms used herein have the same meaning as commonly understood by one of skill in the art to which the disclosure pertains. Although any methods and materials similar to or equivalent to those described herein can be used in the practice or testing of the PYY analogs, pharmaceutical compositions and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Definitions

As used herein, "about" means within a statistically meaningful range of a value or values such as, for example, a stated concentration, length, molecular weight, pH, sequence identity, time frame, temperature, volume, etc. Such a value or range can be within an order of magnitude typically within 20%, more typically within 10%, and even more typically within 5% of a given value or range. The allowable variation encompassed by "about" will depend upon the particular system under study, and can be readily appreciated by one of skill in the art.

As used herein, "amino acid" means a molecule that, from a chemical standpoint, is characterized by the presence of one or more amine groups and one or more carboxylic acid groups and may contain other functional groups. As is known in the art, there is a set of twenty amino acids that are designated as standard amino acids and that are used as building blocks for most of the peptides/proteins produced by any living being.

As used herein, "amino acid with a functional group available for conjugation" means any natural or unnatural amino acid with a functional group that may be conjugated to a fatty acid by way of, for example, a linker. Examples of such functional groups include, but are not limited to, alkynyl, alkenyl, amino, azido, bromo, carboxyl, chloro, iodo and thiol groups. Additionally, examples of natural amino acids including such functional groups include C (thiol), D (carboxyl), E (carboxyl), K (amino) and Q (amide).

As used herein, "analog" means a compound, such as a synthetic peptide or polypeptide, that activates a target receptor and that elicits at least one in vivo or in vitro effect elicited by a native agonist for that receptor.

As used herein, "anorectic effect" means an ability of the PYY analogs herein to reduce appetite, resulting in lower food consumption and ultimately leading to weight loss. Anorectic effect also may refer to an ability of the PYY analogs herein to increase gut motility.

As used herein, "$C_{16}$-$C_{22}$ fatty acid" means a carboxylic acid having between 16 and 22 carbon atoms. The $C_{16}$-$C_{22}$ fatty acid suitable for use herein can be a saturated monoacid or a saturated diacid ("diacids" have a carboxyl group on each end).

As used herein, "AUC" means area under the curve.

As used herein, "effective amount" means an amount, concentration or dose of one or more PYY analogs herein, or a pharmaceutically acceptable salt thereof which, upon single or multiple dose administration to an individual in need thereof, provides a desired effect in such an individual under diagnosis or treatment (i.e., may produce a clinically measurable difference in a condition of the individual such as, for example, a reduction in blood glucose, a reduction in HbA1c, and/or a reduction in weight or body fat). An effective amount can be readily determined by one of skill in the art by using known techniques and by observing results obtained under analogous circumstances. In determining the effective amount for an individual, a number of factors are considered, including, but not limited to, the species of mammal, its size, age and general health, the specific disease or disorder involved, the degree of or involvement or the severity of the disease or disorder, the response of the individual, the particular PYY analog administered, the mode of administration, the bioavailability characteristics of the preparation administered, the dose regimen selected, the use of concomitant medication, and other relevant circumstances.

As used herein, "half-maximal effective concentration" or "$EC_{50}$" means a concentration of compound that results in 50% activation/stimulation of an assay endpoint, such as a dose-response curve (e.g., cAMP).

As used herein, "in combination with" means administering at least one of the PYY analogs herein either simultaneously, sequentially or in a single combined formulation with one or more additional therapeutic agents.

As used herein, "incretin analog" means a peptide or polypeptide having structural similarities with, but multiple differences from, each of GIP, GLP-1, GCG and OXM, especially native, human GIP, GLP-1, GCG and OXM. Some incretin analogs also have affinity for and activity at two or even each of the GIP, GLP-1 and GCG receptors (i.e., agonist activity at two receptors such as in OXM, GIP/GLP-1 or GLP-1/GCG, or even agonist activity at all three receptors).

As used herein, "individual in need thereof" means a mammal, such as a human, with a condition, disease, disorder or symptom requiring treatment or therapy, including for example, those listed herein. In particular, the preferred individual to be treated is a human.

As used herein, "long-acting" means that binding affinity and activity of a PYY analog herein continues for a period of time greater than native, human $PYY_{1-36}$ (SEQ ID NO:1) and/or native, human $PYY_{3-36}$ (SEQ ID NO:2), allowing for dosing at least as infrequently as once daily or even thrice-weekly, twice-weekly, once-weekly, or monthly. The time action profile of the PYY analogs herein may be measured using known pharmacokinetic test methods such as those described in the Examples below.

As used herein, "non-standard amino acid" means an amino acid that may occur naturally in cells but does not participate in peptide synthesis. Non-standard amino acids can be constituents of a peptide and often times are generated by modification of standard amino acids in the peptide (i.e., via post-translational modification). Non-standard amino acids can include D-amino acids, which have an opposite absolute chirality of the standard amino acids above.

As used herein, "obese" or "obesity" means a condition in which an individual has a body mass index (BMI) that is >30.0 kg/m². *See generally*, "Overweight & Obesity" by the Center for Disease Control and Prevention available at cdc.gov/obesity/adult/defining.html; and "Definitions & Facts for Adult Overweight & Obesity" by the National Institutes of Health at iddk.nih.gov/health-information/weight-management/adult-overweight-obesity/definition-facts.

As used herein, "obesity-related disease or disorder" means any diseases or disorders that are induced/exacerbated by obesity including, but not limited to, angina pectoris, cardiovascular disease, cholecystitis, cholelithiasis, congestive heart failure, dyslipidemia, fatty liver disease, fertility complications, glucose intolerance, gout, hypertension, hypothyroidism, hyperinsulinemia, insulin resistance, osteoarthritis, polycystic ovary syndrome (PCOS), pregnancy complications, psychological disorders, sleep apnea and other respiratory problems, stress urinary incontinence stroke, T2DM, uric acid nephrolithiasis (kidney stones), and cancer of the breast, colon, endometrium, esophagus, gall bladder, kidney, prostate and rectum.

As used herein, "overweight" means a condition in which an individual has a BMI that is about 25.0 kg/m² to <30 kg/m². See, id.

As used herein, "PYY" means Peptide YY obtained or derived from any species, such as a mammalian species, especially a human. PYY includes both the native PYY (i.e., full-length) and variations thereof (i.e., additions, deletions and/or substitutions of native PYY). Specific PYYs include, but are not limited to, native, human $PYY_{1-36}$ (SEQ ID NO:1) and native, human $PYY_{3-36}$ (SEQ ID NO:2).

As used herein, "PYY analog" or "PYY analogs" means a PYY-like peptide or polypeptide that elicits one or more effects of native PYY at one or more NPY receptors such as the NPY2 receptor. In some instances, the PYY analogs herein can bind to a NPY receptor, especially the human NPY2 receptor, with higher or lower affinity but demonstrate a longer half-life in vivo or in vitro when compared to native PYY, especially human PYY such as native, human $PYY_{1-36}$ (SEQ ID NO:1) and native, human $PYY_{3-36}$ (SEQ ID NO:2). In this manner, the PYY analogs herein are synthetic compounds that act as NPY2 receptor agonists.

As used herein, "saturated" means the fatty acid contains no carbon-carbon double or triple bonds.

As used herein, "sensitizing effect" means an ability of the PYY analogs herein to increase the effect of insulin and thereby help lower blood glucose.

As used herein, "treating" or "to treat" means attenuating, restraining, reversing, slowing or stopping progression or severity of an existing condition, disease, disorder or symptom.

Certain abbreviations are defined as follows: "ACR" refers to urine albumin/urine creatinine ratio: "amu" refers to atomic mass unit; "tBoc" refers to tert-butoxycarbonyl: "CAMP" refers to cyclic adenosine monophosphate: "DMF" refers to dimethylformamide: "DMSO" refers to dimethyl sulfoxide: "EIA/RIA" refers to enzyme immunoassay/radioimmunoassay: "hr" refers to hour; "HTRF" refers to homogenous time-resolved fluorescent: "IV" refers to intravenous: "kDa" refers to kilodaltons: "LC-MS" refers to liquid chromatography-mass spectrometry: "MS" refers to mass spectrometry: "OtBu" refers to O-tert-butyl: "Pbf" refers to NG-2,2,4,6,7-pentamethyldihydrobenzofuran-5-sulfonyl: "RP-HPLC" refers to reversed-phase high performance liquid chromatography: "SQ" refers to subcutaneous: "SEM" refers to standard error of the mean: "TFA" refers to trifluoroacetic acid; and "Trt" refers to Trityl.

PYY Analogs

The PYY analogs herein have structural similarities to, but many structural differences, from native PYY peptides. For example, when compared to native, human $PYY_{1-36}$ (SEQ ID NO:1) and/or native, human $PYY_{3-36}$ (SEQ ID NO:2), the PYY analogs described herein include modifications at one or more of positions 3, 7, 9, 10, 17, 18, 22, 23, 30 and 31 with respect to the numbering of native, human $PYY_{1-36}$ (SEQ ID NO:1). In certain instances, exemplary amino acid sequences of the PYY analogs herein include (specific changes relative to corresponding residue of native, human PYY (SEQ ID NO:1) are in bold):

(SEQ ID NO: 3)
³PKPEX₇PX₉X₁₀DASPEEX₁₇X₁₈RYYX₂₂X₂₃LRHYLNX₃₀LTRQRY³⁶, (SEQ ID NO: 4)
³PKPEKPGEDASPEEWQRYYAELRHYLNWLTRQRY³⁶, (SEQ ID NO: 5)
³PKPEKPGEDASPEEWQRYYAELRHYLNELTRQRY³⁶, (SEQ ID NO: 6)
³PKPEKPEEDASPEEWQRYYIELRHYLNWLTRQRY³⁶, (SEQ ID NO: 7)
³PKPEKPGKDASPEEWNRYYADLRHYLNWLTRQRY³⁶, and (SEQ ID NO: 8)
³PKPEKPGEDASPEELQRYYASLRHYLNWLTRQRY³⁶.

The PYY analogs herein result in sufficient activity at the human NPY2 receptor but insufficient activity at the NPY1, NPY4 and NPY5 receptors. Likewise, the PYY analogs herein have beneficial attributes relevant to their developability as therapeutic treatments, including improved solubility in aqueous solutions, improved chemical and physical formulation stability, extended pharmacokinetic profile, and minimized potential for immunogenicity.

In some instances, the PYY analogs herein are amidated at a C-terminal amino acid to affect stability. In addition to the changes described herein, the analogs may include one or more additional amino acid modifications, provided, however, that the analogs remain capable of binding to and activating the human NPY2 receptor.

The PYY analogs herein further include a fatty acid conjugated, for example, by way of a linker to a natural or unnatural amino acid with a functional group available for conjugation (i.e., "acylation"). In some instances, the amino acid with a functional group available for conjugation can be C, D, E, K and Q. In particular instances, the amino acid with the functional group available for conjugation is K, where conjugation is to an &-amino group of a K side chain.

Here, acylation of the PYY analogs is at position 7 when compared to native, human $PYY_{1-36}$ (SEQ ID NO:1). In this manner, the fatty acid can act as an albumin binder to provide for longer-acting analogs.

With respect to the fatty acid, it can be chemically conjugated to the functional group of the amino acid available for conjugation either by a direct bond or by a linker. The length and composition of the fatty acid impacts the half-life of the PYY analogs, the in vivo potency of the PYY analogs, and the solubility and stability of the PYY analogs. Conjugation to a $C_{16}$-$C_{22}$ saturated fatty monoacid or diacid thereby results in PYY analogs that exhibit desirable half-life, desirable in vivo potency, and desirable solubility and stability characteristics.

Exemplary saturated $C_{16}$-$C_{22}$ fatty acids for use herein include, but are not limited to, hexadecanoic acid (i.e., palmitic acid, $C_{16}$ monoacid), hexadecanedioic acid ($C_{16}$ diacid), heptadecanoic acid (i.e., margaric acid, $C_{17}$ monoacid), heptadecanedioic acid ($C_{17}$ diacid), stearic acid ($C_{18}$ monoacid), octadecanedioic acid ($C_{18}$ diacid), nonadecylic acid (i.e., nonadecanoic acid, $C_{19}$ monoacid), nonadecanedioic acid ($C_{19}$ diacid), eicosanoic acid (i.e., arachadic acid, $C_{20}$ monoacid), eicosanedioic acid ($C_{20}$ diacid), heneicosanoic acid (i.e., heneicosylic acid, $C_{21}$ monoacid), heneicosanedioic acid ($C_{21}$ diacid), docosanoic acid (i.e., behenic acid, $C_{22}$ monoacid), docosanedioic acid ($C_{22}$ diacid), and branched and substituted derivatives thereof. In certain instances, the $C_{16}$-$C_{22}$ fatty acid can be a saturated $C_{18}$ monoacid, a saturated $C_{18}$ diacid, a saturated $C_{19}$ monoacid, a saturated $C_{19}$ diacid, a saturated $C_{20}$ monoacid, a saturated $C_{20}$ diacid, and branched and substituted derivatives thereof. In particular instances, the $C_{16}$-$C_{22}$ fatty acid can be palmitic acid or hexadeconic acid, stearic acid or octadeconic acid, or arachidic acid or eicosanoic acid.

To assist in conjugating a fatty acid to a natural or unnatural amino acid with the functional group available for conjugation, the PYY analogs herein can include a linker. In some instances, the linker can be at least one of AEEA, Ahx, E or γE, as well as combinations thereof.

When the linker includes the amino acids, it can have one to four E or γE amino acid residues. In some instances, the linker can include one or two E and/or γE amino acid residues. For example, the linker can include either one or two E and/or γE amino acid residues. In other instances, the linker can include one to four amino acid residues (such as, for example, E or γE amino acids) used in combination with AEEA or Ahx. Specifically, the linker can be combinations of E and γE amino acid residues with AEEA or Ahx. In still other instances, the linker can be combinations of one or two γE amino acid residues and one or two AEEA or Ahx. In particular instances, the linker can be an $(AEEA)_2$•γE moiety, an Ahx•E•γE moiety, or an AEEA•γE moiety.

Exemplary linker-fatty acid moieties can include $(AEEA)_2$•γE•$C_{20}$ diacid, Ahx•E•γE•$C_{18}$ diacid, or AEEA•γE•$C_{18}$ diacid. The structural features of these linker-fatty acid moieties result in analogs having improved half-life when compared to native, human $PYY_{1-36}$ (SEQ ID NO:1) or native, human $PYY_{3-36}$ (SEQ ID NO:2).

Taken together, exemplary PYY analogs are:

(SEQ ID NO:9)

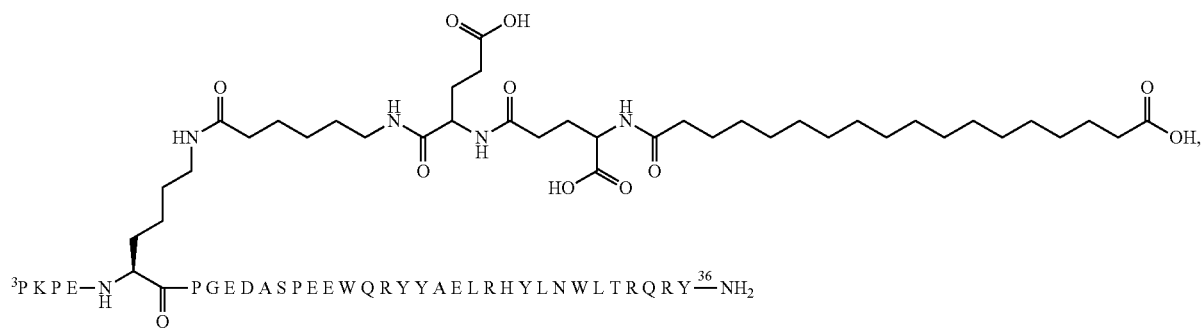

(SEQ ID NO:10)
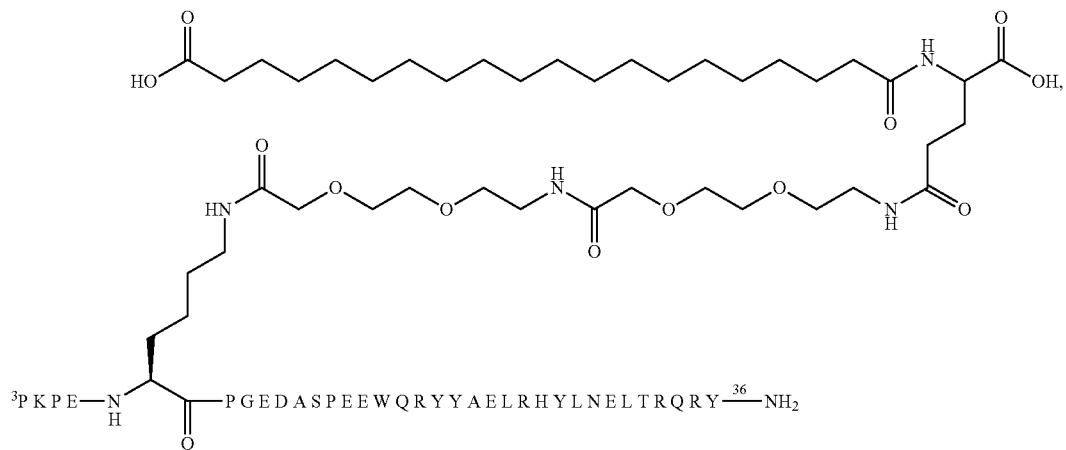
(SEQ ID NO:11)
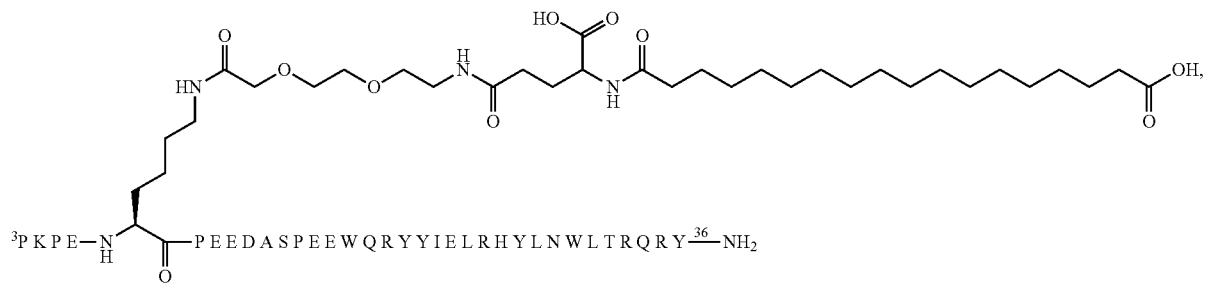
(SEQ ID NO:12)
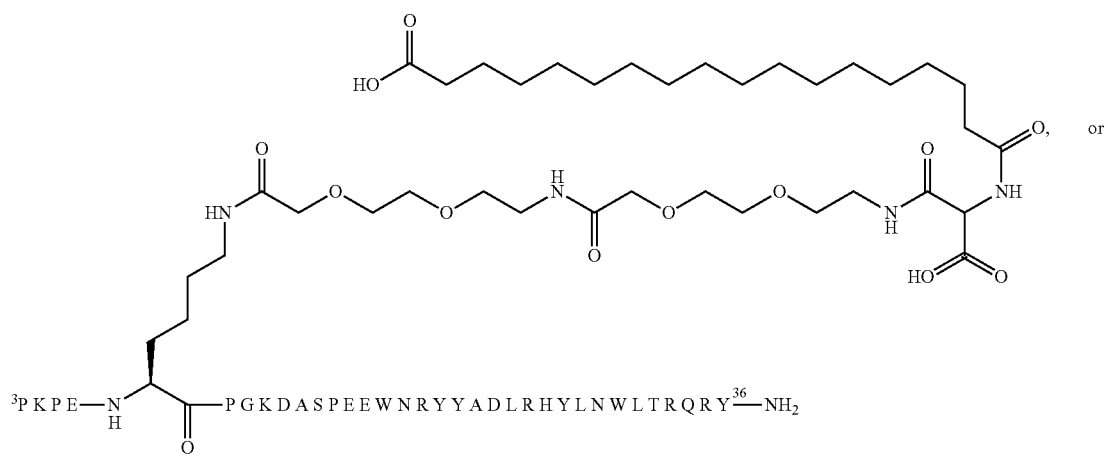

-continued (SEQ ID NO:13)

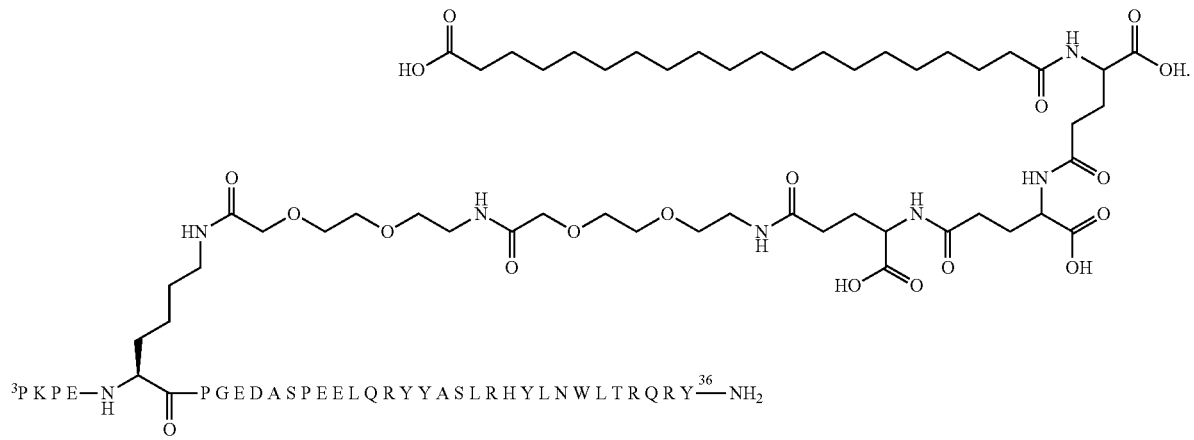

Although the PYY analogs are described as having thirty-four amino acids like that of native, human PYY$_{3-36}$ (SEQ ID NO:2), it is contemplated that the PYY analogs herein can have an amino acid sequence based upon native, human PYY$_{1-36}$ (SEQ ID NO:1). That is, the PYY analogs can include the two N-terminal amino acids (i.e., the "YP" residues of positions 1 and 2 of SEQ ID NO: 1) of native, human PYY$_{1-36}$ (SEQ ID NO:1), which subsequently can be cleaved in vivo when administered to an individual as would occur when native, human PYY$_{1-36}$ (SEQ ID NO:1) is endogenously released.

Half-life of the PYY analogs herein may be measured using techniques known in the art including, for example, those described in the Examples below. Likewise, affinity of the PYY analogs herein for each of the various human NPY receptors (e.g., NPY2R, NPY5R) may be measured using techniques known in the art for measuring receptor binding levels including, for example, those described in the Examples below, and is commonly expressed as an inhibitory constant (Ki) value. Moreover, activity of the PYY analogs herein at each of the receptors also may be measured using techniques known in the art, including, for example, the in vitro activity assays described below, and is commonly expressed as an EC$_{50}$ value.

As a result of the modifications described above, the PYY analogs herein have a half-life that is longer than that of native, human PYY$_{3-36}$ (SEQ ID NO:2). For example, the PYY analogs can have a half-life from about 5 hours to about 24 hours, from about 6 hours to about 23 hours, from about 7 hours to about 22 hours, from about 8 hours to about 21 hours, from about 9 hours to about 20 hours, from about 10 hours to about 19 hours, from about 11 hours to about 18 hours, from about 12 hours to about 17 hours, from about 13 hours to about 16 hours, or even from about 14 hours to about 15 hours. Alternatively, the PPY analogs herein can have a half-life that is about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or even about 24 hours, especially about 12 hours.

Likewise, the PYY analogs herein have a binding affinity at the NPY2 receptor that is greater than that of native, human PYY$_{3-36}$ (SEQ ID NO:2), such as from about 2-fold to about 10-fold. Alternatively, the PYY analogs herein can have a binding affinity up to about 2-fold greater, about 3-fold greater, about 4-fold greater, about 5-fold greater, about 6-fold greater, about 7 fold-greater, about 8-fold greater, about 9-fold greater, or even about 10-fold greater, especially 2-fold greater to 3-fold greater, than that of native, human PYY$_{3-36}$ (SEQ ID NO:2).

Pharmaceutical Compositions

The PYY analogs herein can be formulated as pharmaceutical compositions, which can be administered by parenteral routes (e.g., intravenous, intraperitoneal, intramuscular, subcutaneous or transdermal). Such pharmaceutical compositions and techniques for preparing the same are well known in the art. See, e.g., Remington, "The Science and Practice of Pharmacy" (D. B. Troy ed., 21$^{st}$ Edition, Lippincott, Williams & Wilkins, 2006). In particular instances, the PYY analogs are administered SQ. Alternatively, however, the PYY analogs can be formulated in forms for other pharmaceutically acceptable routes such as, for example, tablets or other solids for oral administration: time release capsules; and any other form currently used, including creams, lotions, inhalants and the like.

To improve their in vivo compatibility and effectiveness, the PYY analogs herein may be reacted with any of a number of inorganic and organic acids/bases to form pharmaceutically acceptable acid/base addition salts. Pharmaceutically acceptable salts and common methodologies for preparing them are well known in the art (see, e.g., Stahl et al., "Handbook of Pharmaceutical Salts: Properties, Selection and Use," 2nd Revised Edition (Wiley-VCH, 2011)). Pharmaceutically acceptable salts for use herein include sodium, trifluoroacetate, hydrochloride and acetate salts.

The PYY analogs herein may be administered by a physician or self-administered using an injection. It is understood the gauge size and amount of injection volume can be readily determined by one of skill in the art. However, the amount of injection volume can be≤ about 2 mL or even≤ about 1 mL, and the needle gauge can be ≥ about 27 G or even ≥ about 29 G.

The disclosure also provides and therefore encompasses novel intermediates and methods useful for synthesizing the PYY analogs herein, or a pharmaceutically acceptable salt thereof. The intermediates and PYY analogs herein can be prepared by a variety of methodologies that are well known in the art. For example, a method using chemical synthesis is illustrated in the Examples below. The specific synthetic steps for each of the routes described may be combined in different ways to prepare the PYY analogs described herein. The reagents and starting materials are readily available to one of skill in the art.

The PYY analogs herein are generally effective over a wide dosage range. Exemplary doses of the PYY analogs herein or of pharmaceutical compositions including the same can be milligram (mg), microgram (μg), nanogram (ng) or picogram (pg) amounts per kilogram (kg) of an individual. In this manner, a daily dose can be from about 1 μg to about 100 mg.

Here, the effective amount of the PYY analog in a pharmaceutical composition can be a dose of about 0.25 mg to about 5.0 mg. One of skill in the art, however, understands that in some instances the effective amount (i.e., dose/dosage) may be below the lower limit of the aforesaid range and be more than adequate, while in other cases the effective amount may be a larger doses and may be employed with acceptable side effects.

In addition to the PYY analog, the pharmaceutical composition also can include an additional therapeutic agent, especially other antidiabetic or weight loss agents. In some instances, the additional therapeutic agent can be at least one of an incretin or a DPP-IV inhibitor. Exemplary incretins include, but are not limited to, GCG, GLP-1, GLP-1 (7-36)$_{amide}$, GIP, OXM, a GCG analog, a GLP-1 analog, a GIP analog, an OXM analog, a GIP/GLP-1, a GLP-1/GCG, or even an incretin analog having triple receptor activity.

In this manner, the pharmaceutical composition can include an effective amount of a PYY analog of SEQ ID NO:9 and an incretin or a DPP-IV inhibitor, an effective amount of a PYY analog of SEQ ID NO:10 and an incretin or a DPP-IV inhibitor, an effective amount of a PYY analog of SEQ ID NO: 11 and an incretin or a DPP-IV inhibitor, an effective amount of a PYY analog of SEQ ID NO:12 and an incretin or a DPP-IV inhibitor, or an effective amount of a PYY analog of SEQ ID NO: 13 and an incretin or a DPP-IV inhibitor.

In those instances in which the incretin is GLP-1 or a GLP-1 analog, it can be GLP-1 or a GLP-1 analog such as albiglutide, dulaglutide, liraglutide, semaglutide, or combinations thereof, especially dulaglutide.

Methods of Making and Using the PYY Analogs

The PYY analogs herein can be synthesized via any number of peptide synthesis methods known in the art using standard manual or automated solid-phase synthesis procedures. Automated peptide synthesizers are commercially available from, for example, Applied Biosystems (Foster City, CA) and Protein Technologies Inc. (Tucson, AZ). Reagents for solid-phase synthesis are readily available from commercial sources. Solid-phase synthesizers can be used according to the manufacturer's instructions for blocking interfering groups, protecting amino acids during reaction, coupling, deprotecting and capping of unreacted amino acids.

Typically, an N-α-carbamoyl-protected amino acid and the N-terminal amino acid on the growing peptide chain attached to a resin are coupled at room temperature in an inert solvent such as DMF, N-methylpyrrolidone or methylene chloride in the presence of coupling agents such as diisopropyl-carbodiimide and 1-hydroxybenzotriazole. The N-α-carbamoyl protecting group is removed from the resulting peptide resin using a reagent such TFA or piperidine, and the coupling reaction is repeated with the next desired N-α-protected amino acid to be added to the peptide chain. Suitable amine protecting groups are well known in the art and are described, for example, in Green & Wuts, "Protecting Groups in Organic Synthesis," (John Wiley and Sons, 1991). The most commonly used examples include tBoc and Fmoc. After completion of synthesis, peptides are cleaved from the solid-phase support with simultaneous side chain deprotection using standard treatment methods under acidic conditions.

One of skill in the art will appreciate that the peptide chains described herein are synthesized with a C-terminal carboxamide. For the synthesis of C-terminal amide peptides, resins incorporating Rink amide MBHA or Rink amide AM linkers typically are used with Fmoc synthesis, while MBHA resin is generally used with tBoc synthesis.

Crude peptides typically are purified using RP-HPLC on C8 or C18 columns using water-acetonitrile gradients in 0.05% to 0.1% TFA. Purity can be verified by analytical RP-HPLC. Identity of peptides can be verified by MS. Peptides can be solubilized in aqueous buffers over a wide pH range.

One use of the PYY analogs herein is for reducing blood glucose and/or body weight in individuals, especially individuals who are overweight or obese and have T2DM. Administering a PYY analog as described herein can result in glycemic control by improving insulin sensitization and weight loss. As such, the PYY analogs herein show glucose lowering efficacy with the added benefit of weight reduction, such that individuals can delay progression to insulin and maintain target HbA1c goals.

The methods can include the steps described herein, and these may be be, but not necessarily, carried out in the sequence as described. Other sequences, however, also are conceivable. Moreover, individual or multiple steps bay be carried out either in parallel and/or overlapping in time and/or individually or in multiply repeated steps. Furthermore, the methods may include additional, unspecified steps.

Such methods therefore can include selecting an individual who is overweight and has T2DM or is predisposed to the same. Alternatively, the methods can include selecting an individual who is obese and has T2DM or is predisposed to the same.

The methods also can include administering to the individual an effective amount of at least one PYY analog as described herein, which may be in the form of a pharmaceutical composition as also described herein. In some instances, the at least one PYY analog/pharmaceutical composition can include an additional therapeutic agents such as an incretin or a DPP-IV inhibitor.

The concentration/dose/dosage of the at least one PYY analog and optional incretin or DPP-IV inhibitor are discussed elsewhere herein.

With regard to a route of administration, the at least one PYY analog or pharmaceutical composition including the same can be administered in accord with known methods such as, for example, orally: by injection (i.e., intra-arterially, intravenously, intraperitoneally, intracerebrally, intracerebroventricularly, intramuscularly, intraocularly, intraportally or intralesionally): by sustained release systems, or by implantation devices. In certain instances, the at least one PYY analog or pharmaceutical composition including the same can be administered SQ by bolus injection or continuously.

With regard to a dosing frequency, the at least one PYY analog or pharmaceutical composition including the same can be administered daily, every other day, three times a week, two times a week, one time a week (i.e., weekly), biweekly (i.e., every other week), or monthly. In certain instances, the at least one PYY analog or pharmaceutical composition including the same is administered SQ every other day, SQ three times a week, SQ two times a week, SQ one time a week, SQ every other week or SQ monthly. In particular instances, the at least one PYY analog or pharmaceutical composition including the same is administered SQ one time a week (QW).

Alternatively, the at least one PYY analog or pharmaceutical composition including the same can be orally administered. As above, and with regard to dosing frequency, the at least one PYY analog or pharmaceutical composition including the same can be administered daily, every other day, three times a week, two times a week, one time a week (i.e., weekly), biweekly (i.e., every other week), or monthly. In certain instances, the at least one PYY analog or pharmaceutical composition including the same is administered orally every other day, orally three times a week, orally two times a week, orally one time a week, or orally every other week. In particular instances, the PYY analog is administered orally one time a week.

With regard to those instances in which the at least one PYY analog or pharmaceutical composition including the same is administered in combination with an effective amount of an incretin, the incretin can be GCG or a GCG analog, GLP-1, GLP-1 (7-36)$_{amide}$ or a GLP-1 analog, GIP or a GIP analog, OXM or an OXM analog, GIP/GLP-1, GLP-1/GCG, or even an incretin having triple receptor activity. The GCG, GCG analog, GLP-1, GLP-1 (7-36)$_{amide}$, GLP-1 analog, GIP, GIP analog, OXM, OXM analog, GIP/GLP-1, GLP-1/GCG, or incretin having triple receptor activity can be administered simultaneously, separately or sequentially with the at least one PYY analog or pharmaceutical composition including the same.

Moreover, the GCG, GCG analog, GLP-1, GLP-1 (7-36)$_{amide}$, GLP-1 analog, GIP, GIP analog, OXM, OXM analog, GIP/GLP-1, GLP-1/GCG, or incretin having triple receptor activity can be administered with a frequency same as the at least one PYY analog or pharmaceutical composition including the same (i.e., every other day, twice a week, or even weekly). Alternatively, the GCG, GCG analog, GLP-1, GLP-1 (7-36)$_{amide}$, GLP-1 analog. GIP, GIP analog, OXM, OXM analog, GIP/GLP-1, GLP-1/GCG, or incretin having triple receptor activity can be administered with a frequency distinct from the at least one PYY analog or pharmaceutical composition including the same. In other instances, the GCG, GCG analog, GLP-1, GLP-1 (7-36)$_{amide}$, GLP-1 analog, GIP, GIP analog, OXM, OXM analog, GIP/GLP-1, GLP-1/GCG, or incretin having triple receptor activity is administered QW. In still other instances, the PYY analog is administered SQ, and the GCG, GCG analog, GLP-1, GLP-1 (7-36)$_{amide}$, GLP-1 analog, GIP, GIP analog, OXM, OXM analog, GIP/GLP-1, GLP-1/GCG, or incretin having triple receptor activity can be administered orally.

It is further contemplated that the methods may be combined with diet and exercise and/or may be combined with additional therapeutic agents other than those discussed above.

EXAMPLES

The following non-limiting examples are offered for purposes of illustration, not limitation.

Example 1: PYY Analog 1

One PYY analog incorporating the inventive concept can have a structure of:

(SEQ ID NO: 9)

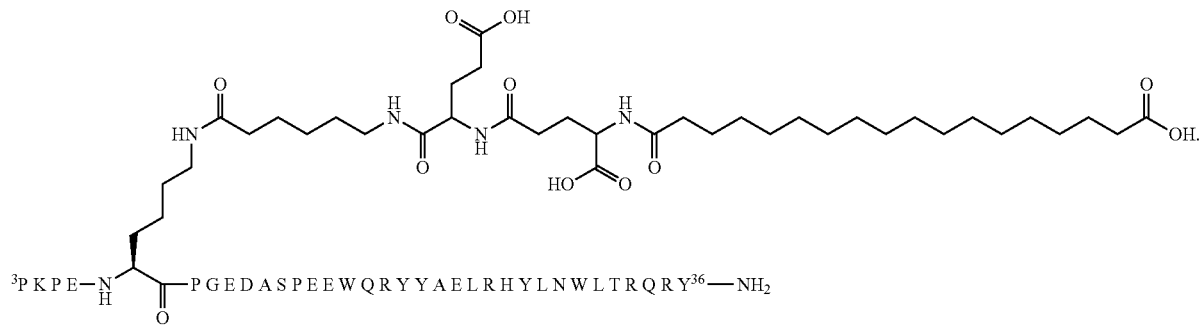

Here, the N-terminus is free, and the C-terminal amino acid is amidated as a C-terminal primary amide. The K at position 7 is chemically modified through conjugation to the ε-amino group of the K side chain at position 7 with (Ahx-E-(γE)—CO—(CH$_2$)$_{16}$—COOH.

The PYY analog according to SEQ ID NO:9 is generated by solid-phase peptide synthesis using Fmoc/t-Bu strategy on a Symphony X Automated Peptide Synthesizer (PTI Protein Technologies Inc.) starting from RAPP AM-Rink Amide resin (H40023 Polystyrene AM RAM, Rapp polymere GmbH). Amino acid couplings are performed using 10 equivalents of amino acid, 0.9 M diisopropylcarbodiimide (DIC) and 0.9 M Oxyma (1:1:1 molar ratio) in DMF for 3h at 25° C. Deprotections are carried out using 25% piperidine solutions in DMF.

After elongating the peptide-resin as described above, the MTT protecting group present in K at position 7 is removed using 30% Hexafluoroisopropanol (HFIP) in dichloromethane (DCM). Additional coupling/deprotection cycles using a Fmoc/t-Bu strategy to extend the K at position 7 side chain involve Fmoc-6-aminohexanoic acid (Chem-Impex International Catalog #02490), Fmoc-Glu(OtBu)-OH, Fmoc-Glu (OH)-OtBu (ChemPep Catalog #100703) and HOOC—(CH$_2$)$_{16}$—COOtBu. In all couplings, 3 equivalents of the building block are used with PyBOP (3 equiv) and DIEA (6 equiv) in DMF for 3 h at 25° C.

Concomitant cleavage from the resin and side chain protecting group removal are carried out in a solution containing TFA:triisopropylsilane:1,2-ethanedithiol:methanol:thioanisole 80:5:5:5:5 (v/v) for 2 h at 25° C. followed by precipitation with cold ether. Crude peptide is purified to >99% purity (15-20% purified yield) by RP-HPLC on a Phenyl Hexyl Column (Phenomenex, Luna: 5 μm, 100A), where suitable fractions are pooled and lyophilized.

The purity of the PYY analog is examined by analytical RP-HPLC, and identity is confirmed using LC/MS (observed: M+3H$^+$/3=1659.2 (+/−0.2); calculated: M+3H$^+$/3 = 1659.2; observed: M+4H$^+$/4=1244.6 (+/−0.2); calculated: M+4H$^+$/4=1244.6; observed: M+5H$^+$/5=995.9 (+/−0.2); calculated: M+5H$^+$/5=995.9).

Example 2: PYY Analog 2

One PPY analog incorporating the inventive concept can have a structure of:

(SEQ ID NO: 10)

$^3$P K P E—N(H)—PGEDASPEEWQRYYAELRHYLNELTRQRY$^{36}$—NH$_2$

As in Example 1, the N-terminus is free, and the C-terminal amino acid is amidated as a C-terminal primary amide. In contrast, however, the K at position 7 is chemically modified through conjugation to the ε-amino group of the K side chain with ([2-(2-amino-ethoxy)-ethoxy]-acetyl)$_2$-(γE)—CO—(CH$_2$)$_{18}$—COOH.

The PYY analog according to SEQ ID NO: 10 is generated by solid-phase peptide, similar to that described above in Example 1. Thus, FMOC-NHPEG$_2$—CH$_2$COOH and HOOC—(CH$_2$)$_{18}$—COOtBu is attached to the side chain after MTT cleavage using 3 equivalents of the building block with PyBOP (3 equiv) and DIEA (6 equiv) in DMF for 3 h at 25° C.

The purity of the PYY analog is examined by analytical RP-HPLC, and identity is confirmed using LC/MS (observed: M+3H$^+$/3=1665.4 (+/−0.2); calculated: M+3H$^+$/3 = 1665.5: observed: M+4H$^+$/4=1249.3 (+/−0.2); calculated M+4H$^+$/4=1249.4; observed: M+5H$^+$/5=999.7 (+/−0.2); calculated: M+5H$^+$/5=999.7).

Example 3: PYY Analog 3

One PYY analog incorporating the inventive concept can have a structure of:

(SEQ ID NO: 11)

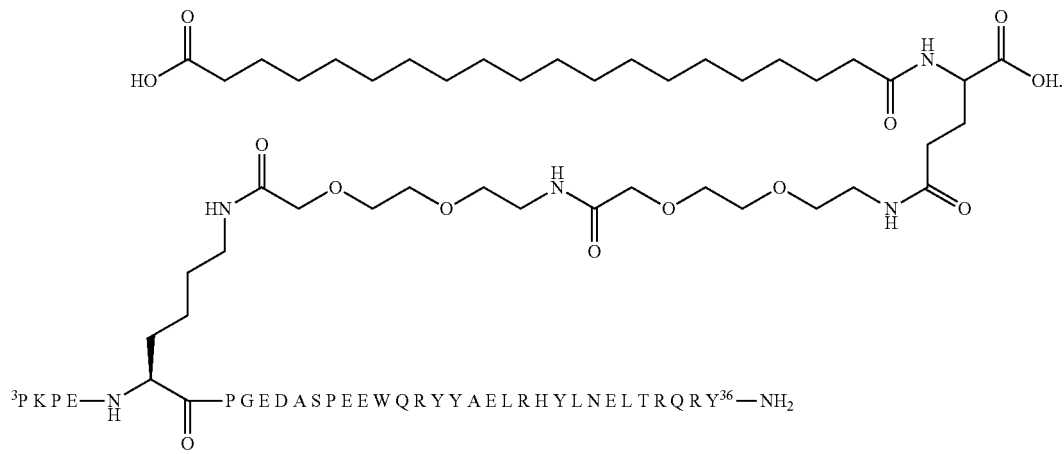

$^3$P K P E—N(H)—PEEDASPEEWQRYYIELRHYLNWLTRQRY$^{36}$—NH$_2$

As in Example 1, the N-terminus is free, and the C-terminal amino acid is amidated as a C-terminal primary amide. In contrast, however, the K at position 7 is chemically modified through conjugation to the ε-amino group of the K side chain with ([2-(2-amino-ethoxy)-ethoxy]-acetyl)-(γE)—CO—(CH$_2$)$_{16}$—COOH.

The PYY analog according to SEQ ID NO:11 is generated by solid-phase peptide, similar to that as described above in Example 1. Thus, FMOC-NHPEG$_2$—CH$_2$COOH and HOOC—(CH$_2$)$_{16}$—COOtBu are attached to the side chain after MTT cleavage using 3 equivalents of the building block with PyBOP (3 equiv) and DIEA (6 equiv) in DMF for 3 h at 25° C.

The purity of the PYY analog is examined by analytical RP-HPLC, and identity is confirmed using LC/MS (observed: M+3H$^+$/3=1664.7 (+/−0.2); calculated: M+3H$^+$/3 = 1664.9: observed: M+4H$^+$/4=1248.9 (+/−0.2); calculated: M+4H$^+$/4=1248.9; observed: M+5H$^+$/5=999.3 (+/−0.2); calculated: M+5H$^+$/5=999.3).

Example 4: PYY Analog 4

One PYY analog incorporating the inventive concept can have a structure of:

above in Example 1. Thus, FMOC-NHPEG$_2$—CH$_2$COOH and HOOC—(CH$_2$)$_{16}$—COOtBu are attached to the side chain after MTT cleavage using 3 equivalents of the building block with PyBOP (3 equiv) and DIEA (6 equiv) in DMF for 3 h at 25° C.

The purity of the PYY analog is examined by analytical RP-HPLC, and identity is confirmed using LC/MS (observed: M+3H$^+$/3=1664.8 (+/−0.2); calculated: M+3H$^+$/3 = 1665.5; observed: M+4H$^+$/4=1248.9 (+/−0.2); calculated:

(SEQ ID NO: 12)

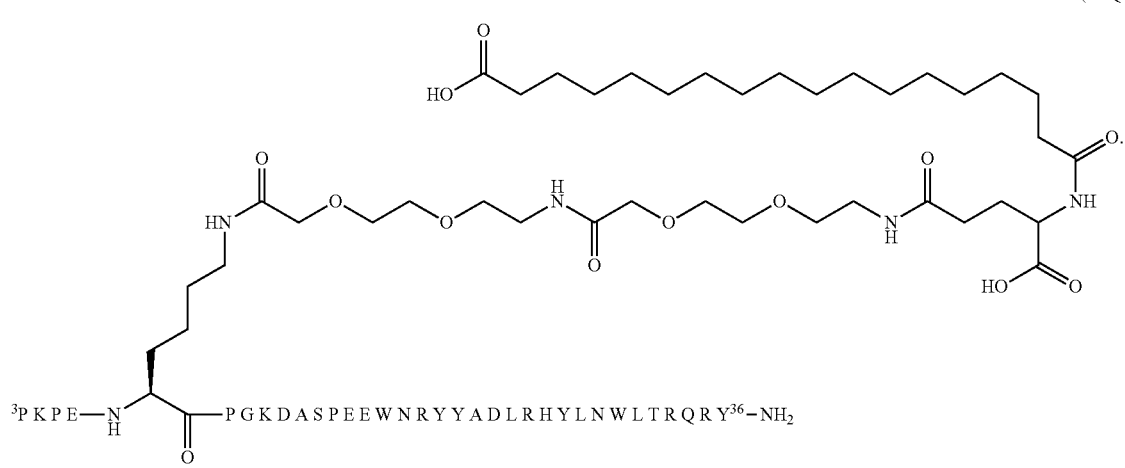

As in Example 1, the N-terminus is free, and the C-terminal amino acid is amidated as a C-terminal primary amide. In contrast, however, the K at position 7 is chemically modified through conjugation to the ε-amino group of the K side chain with ([2-(2-amino-ethoxy)-ethoxy]-acetyl)$_2$-(γE)—CO—(CH$_2$)$_{16}$—COOH.

The PYY analog according to SEQ ID NO: 12 is generated by solid-phase peptide, similar to that as described M+4H$^+$/4=1249.4; observed: M+5H$^+$/5=998.9 (+/−0.2); calculated: M+5H$^+$/5=995.7).

Example 5: PYY Analog 5

One PYY analog incorporating the inventive concept can have a structure of:

(SEQ ID NO: 13)

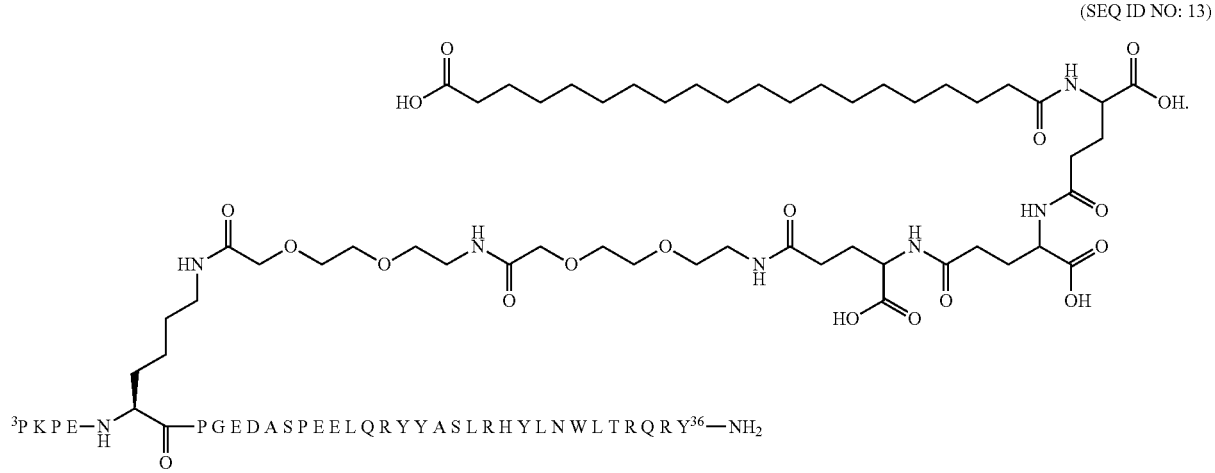

As in Example 1, the N-terminus is free, and the C-terminal amino acid is amidated as a C-terminal primary amide. In contrast, however, the K at position 7 is chemically modified through conjugation to the ε-amino group of the K side chain with ([2-(2-amino-ethoxy)-ethoxy]-acetyl)$_2$-(γE)$_3$—CO—(CH$_2$)$_{18}$—COOH.

The PYY analog according to SEQ ID NO: 13 is generated by solid-phase peptide, similar to that as described above in Example 1. Thus, FMOC-NHPEG$_2$—CH$_2$COOH and HOOC—(CH$_2$)$_{18}$—COOtBu are attached to the side chain after MTT cleavage using 3 equivalents of the building block with PyBOP (3 equiv) and DIEA (6 equiv) in DMF for 3 h at 25° C.

The purity of the PYY analog is examined by analytical RP-HPLC, and identity is confirmed using LC/MS (observed: M+3H$^+$/3=1732.2 (+/−0.2); calculated: M+3H$^+$/3 = 1732.3: observed: M+4H$^+$/4=1299.4 (+/−0.2); calculated: M+4H$^+$/4=1299.5: observed: M+5H$^+$/5=1039.7 (+/−0.2); calculated: M+5H$^+$/5=1039.8).

Example 6: In Vitro Activity of PYY Analogs (1) In vitro binding to hNPY1, hNPY2, hNPY4, and hNPY5 receptors
Purpose:
To assess the in vitro binding affinity (Ki) of the PYY analogs of Examples 1 to 5 in the absence of bovine serum albumin (BSA) to the following human (h) receptors: hNPY1R, hNPY2R, hNPY4R and hNPY5R. Competitive radioligand binding assays with membranes prepared from cell lines overexpressing each of the recombinant receptors and the relevant [$^{125}$I]-labeled peptides are used in a scintillation proximity assay (SPA) method. The binding affinity for the associated native peptides, PYY$_{1-36}$ (SEQ ID NO:1), PYY$_{3-36}$ (SEQ ID NO:2) and Pancreatic Polypeptide$_{1-36}$ (PP$_{1-36}$: SEQ ID NO:14), is determined in each assay as a control.

Methods:
PYY analogs, native, human PYY$_{1-36}$ and control PYY$_{3-36}$ are synthesized at Lilly Research Laboratories (Indianapolis, IN, USA) and are characterized by LC/MS, NMR, and LC/UV analysis (99.5% purity). Peptide contents are estimated at 80% powder mass. The peptides are prepared as 10 mM stock solution in 100% DMSO and kept frozen at −20° C. until just prior to testing in the assays.

For hNPY1R, transient overexpression is performed using CHO cells. Stably transfected cell lines are prepared for hNPY2R and hNPY4R by subcloning receptor cDNA into pcDNA3.1 expression plasmid and transfecting into human embryonic kidney (HEK) 293 cells followed by selection with Geneticin. hNPY5R cloning is performed at Multispan, Inc. (Hayward, CA).

For the preparation of hNPY1R, hNPY2R, mNPY2R and hNPY4R crude cell membranes, two different methods (described below) are utilized. hNPY5R membranes are purchased from Multipan, Inc. (#MCG1275).

Method 1—For hNPY2R and hNPY4R membranes, frozen cell pellets are lysed on ice in 10 mL hypotonic homogenization buffer containing 50 mM Tris HCl, pH 7.5, and Roche Complete™ Protease Inhibitors with EDTA (#1169749001) per gram of wet cell paste. The cell suspension is disrupted using a glass Potter-Elvehjem homogenizer fitted with a Teflon® pestle for 25 strokes. The homogenate is centrifuged at 4° C. at 1100×g for 10 minutes. The supernatant is collected and stored on ice while the pellets are resuspended in homogenization buffer and rehomogenized as described above. The homogenate is centrifuged at 1100×g for 10 minutes. The second supernatant is combined with the first supernatant and centrifuged at 35000×g for 1 hour at 4° C. The resulting membrane pellet is resuspended in homogenization buffer containing protease inhibitors at approximately 1 to 3 mg/mL, quick frozen in liquid nitrogen, and stored as aliquots in a −80° ° C. freezer until use. Protein concentration is determined using a BCA protein assay kit (Pierce, #23225) with BSA as a standard.

Method 2—For hNPY1R membranes, frozen cell pellets are lysed on ice in 5 mL hypotonic homogenization Buffer containing 25 mM Tris HCl, pH 7.5, 1 mM MgCl$_2$, 25 units/mL DNase I (Invitrogen, #18047-019) and Roche Complete™ Protease Inhibitors without EDTA (#11836170001) per gram of wet cell paste. The cell suspension is disrupted using a glass Potter-Elvehjem homogenizer fitted with a Teflon R; pestle for 25 strokes. The homogenate is centrifuged at 4° C. at 1800×g for 15 minutes in a 50 mL conical tube. The supernatant is collected and stored on ice while the pellets are resuspended in homogenization buffer and rehomogenized as described above, except DNase I is not used in the homogenization buffer. The homogenate is centrifuged at 1800×g for 15 minutes. The second supernatant is combined with the first supernatant and centrifuged at 25000×g for 30 minutes at 4° C. The resulting membrane pellet is resuspended in homogenization buffer containing protease inhibitors at approximately 2 mg/mL, aliquoted, and stored in a −80° C. freezer until use. Protein concentration is determined using a BCA protein assay kit (Pierce, #23225) with BSA as a standard.

General binding assay methods—The equilibrium dissociation constants (K$_d$) for the various receptor/radioligand interactions are determined from saturation binding analysis using the same reagents and buffers as described below for compound testing. The K$_d$ values determined for the receptor preparations used in this study are as follows: hNPY2R. 0.0047 nM: hNPY1R, 0.07 nM: hNPY4R. 0.084 nM; and hNPY5R, 0.896 nM.

hNPY1R receptor binding protocol—The receptor binding affinity (Ki) of PYY analog peptides and PYY$_{1-36}$ for hNPY1R is determined from a competitive radioligand binding assay with human recombinant [125I]-PYY$_{1-36}$ (#NEX341, 2200 Ci/mmol) obtained from Perkin Elmer (Waltham, MA). The assay is performed with a SPA method using polyvinyltoluene (PVT) wheat germ agglutinin-coupled SPA beads (#RPNQ0001, Perkin Elmer). Assay buffer (25 mM HEPES, pH 7.5, 1 mM MgCl$_2$, 2.5 mM CaCl$_2$), and 0.2% w/v Bacitracin (RPI, #32000)) is used for preparation of reagents. PYY analogs and PYY$_{1-36}$ are thawed and 3-fold serially diluted in 100% DMSO (10 point concentration response curves) using a Tecan Evo liquid handler. A 20-fold step-down dilution of peptide into assay buffer is made to reduce the level of DMSO and peptide concentration prior to addition into the assay plate. Next, 5 μL serially diluted peptide or DMSO is transferred into a Corning R: 3632 clear bottom assay plate containing 45 μL assay buffer or unlabeled PYY$_{1-36}$ control (nonspecific binding or NSB, at 10 nM final concentration). Then, 50 μL [$^{125}$I]-PYY$_{1-36}$ (0.05 nM final concentration) and 50 μL hNPY1R membranes (1.0 μg/well) are added. The final addition is 50 μL of WGA SPA beads (50 μg/well). Final DMSO concentration are 0).125%. Plates are sealed and mixed on a plate shaker (setting 6) for 1 minute and read with a PerkinElmer Trilux MicroBeta(R scintillation counter after 10 hours of incubation/bead settling time at room temperature. Final assay concentration ranges for peptides tested in response curves are: PYY analogs (2.5 μM to 0.13 nM) and PYY$_{1-36}$ (10 nM to 0.5 μM).

hNPY2 receptor binding protocol—The receptor binding affinity (Ki) of PYY analog peptides and $PP_{1-36}$ for hNPY2R is determined from a competitive radioligand binding assay as described above for hNPY1R. Final assay concentration ranges for peptides tested in response curves are: PYY analogs (0.1 μM to 5 PM) and $PYY_{3-36}$ (10 nM to 0.5 μM).

hNPY4R receptor binding protocol—The receptor binding affinity (Ki) of PYY analog peptides and $PP_{1-36}$ for hNPY4R is determined from a competitive radioligand binding assay as described above for hNPY1R. Final assay concentration ranges for peptides tested in response curves are: PYY analogs (2.5 μM to 0.13 nM) and $PYY_{1-36}$ (10 nM to 0.5 μM).

hNPY5R receptor binding protocol—The receptor binding affinity (Ki) of PYY analog peptides and $PYY_{1-36}$ for hNPY5R is determined from a competitive radioligand binding assay as described above for hNPY1R. Final assay concentration ranges for peptides tested in response curves are: PYY analogs (1 μM to 10 μM) and $PYY_{1-36}$ (1 μM to 10 μM).

Data analysis for NPY receptor binding assays—Raw count per minute (CPM) data for concentration curves of PYY analogs, $PYY_{1-36}$, $PYY_{3-36}$, or $PP_{1-36}$ are converted to percent specific inhibition by subtracting nonspecific binding (NSB, binding in the presence of excess unlabeled $PYY_{1-36}$, $PYY_{3-36}$, or $PP_{1-36}$, respectively) from the individual CPM values and dividing by the total binding signal, also corrected by subtracting nonspecific binding, as shown in the equation below:

% Specific Inhibition =

$$100 - \left[\frac{CPM \text{ for Analog or Control} - CPM \text{ for NSB}}{CPM \text{ for Total Binding} - CPM \text{ for NSB}} \times 100\right].$$

Data are analyzed using four-parameter (curve maximum, curve minimum, $IC_{50}$, Hill slope) nonlinear regression routines (Genedata Screener, version 13.0.5, Genedata AG, Basal, Switzerland). The affinity ($K_i$) is calculated from the relative $IC_{50}$ value based upon the equation $K_i = IC_{50}/(1+D/K_d)$ where D=the concentration of radioligand in the experiment, $IC_{50}$ is the concentration causing 50% inhibition of binding, and $K_d$ is the equilibrium binding affinity constant of the radioligand determined from saturation binding analysis (listed above). A qualifier (>) indicates that the data did not reach 50% inhibition, compared to maximum binding in the absence of competitor, whereby the $K_i$ is calculated using the highest concentration of the compound tested in the assay.

Reported values for $K_i$ are calculated as the geometric mean as shown below: Geometric Mean= $10^{(Arithmetic\ Mean\ of\ Log\ 10\ Ki\ Values)}$.

Standard error of the mean (SEM) is calculated using the delta method as shown below:

$$SEM = \text{Geometric Mean} \times \frac{SD \text{ of log transformed data}}{\text{Square root of } n} \times \ln(10),$$

where SD is the standard deviation, n is the number of independent runs, and ln(10) is the natural logarithm of 10.

Selectivity of peptides for hNPY2R (Y2) versus hNPY5R (Y5), hNPY4R (Y4), and/or hNPY1R (Y1) are calculated by dividing by the hNPY2R results in nM.

Results:

TABLE 1

In Vitro Binding ($K_i$) to hNPY1R, hNPY2R, hNPY4R and hNPY5R.

| Peptide | hNPY2R (nM) | hNPY5R (nM) | hNPY4R (nM) | hNPY1R (nM) | Fold (Y5/Y2) | Fold (Y4/Y2) | Fold (Y1/Y2) |
|---|---|---|---|---|---|---|---|
| $PP_{1-36}$ | — | — | 0.07 | — | — | — | — |
| $PYY_{1-36}$ | 0.007 | 0.37 | 5 | 0.06 | 52 | 714 | 8.6 |
| $PYY_{3-36}$ | 0.008 | 3.6 | 27 | 7 | 450 | 3375 | 875 |
| Example 1 | 0.011 | 59 | 626 | 256 | 5363 | 56909 | 23272 |
| Example 2 | 0.070 | >1000 | >1840 | >1460 | >14285 | >26286 | >20857 |
| Example 3 | 0.009 | 36.4 | 112 | >1550 | 4044 | 12444 | >193750 |
| Example 4 | 0.005 | ND | 280 | >148 | NA | 56000 | >29600 |
| Example 5 | 0.030 | ND | 560 | >1530 | NA | 18666 | >51000 |
| Ref. 1* | 0.016 | 189 | — | — | 11812 | — | — |
| Ref. 2* | 0.021 | 112 | — | — | 5333 | — | — |
| Ref. 3* | 0.013 | 469 | — | — | 36076 | — | — |

*Known PYY analog for comparison; see, Intl. Patent Application Publication No. WO 2016/198682, where Ref. 1 corresponds to Compound 4 therein, Ref. 2 corresponds to Compound 21 therein, and Ref. 3 corresponds to Compound 32 therein.
ND-not detected
NA-not applicable As shown above, the PYY analogs of Examples 1-5 are highly selective for the hNPY2 receptor, even demonstrating reduced binding affinity to hNPY5, hNPY4 and hNPY1 receptors versus native, human $PYY_{3-36}$ (SEQ ID NO:2).

(2) In vitro cAMP activity on the human NPY2 receptor
Purpose:
To determine the in vitro functional activity of the PYY analogs of Examples 1 to 5 compared to native, human $PYY_{3-36}$ by measuring inhibition of forskolin-induced intracellular cAMP production in HEK 293 cells overexpressing the recombinant human NPY2 receptor.
Methods:
PYY analogs and human $PYY_{3-36}$ (SEQ ID NO:2) are synthesized, characterized and stored as described above in the receptor binding assays.

Receptor cloning—A stably transfected cell line is prepared hNPY2 receptor by subcloning receptor cDNA into pcDNA3.1 expression plasmid and transfecting it into HEK 293 cells followed by selection with Geneticin. Aliquots of cells ($1 \times 10^7$ cells/mL) at passage 9 are made and kept frozen in the vapor phase of a liquid nitrogen tank. These frozen aliquots are used at the time of the assay. Cells maintain greater than 95% viability over several months.

hNPY2R CAMP assay—Inhibition of forskolin-induced CAMP production by PYY analogs or $PYY_{3-36}$ is measured using HEK 293 cells overexpressing recombinant hNPY2R. Frozen aliquots of cells are thawed in a 37° C. water bath. Cells are transferred to a 50 mL tube with 10 mL of culture medium (MEM cell culture medium from Life Tech 11090-081 with 10% FBS from Life Tech 10082-147, 1 mM L-Glutamine from Life Tech 25030-081, 1×NEAA from Life Tech 11140-050, 1 mM sodium pyruvate from Life Tech 11360-070, 1× antibiotics-antimycotics from Life Tech 15240-062) and are centrifuged 5 minutes at 1500 rpm in a Beckman tabletop centrifuge. The supernatant is removed and the cell pellet is resuspended in 10 mL of cell culture medium followed by passage through a 40 μm strainer. An accurate count of cell number and cell viability is determined using a Vi-Cell Analyzer from Beckman-Coulter (Vi-Cell XR 2.03). 8000 cells per well are plated into a white 384 well assay plate (Corning, Poly-D-Lysine coated, white/opaque, cat #356661) using a Combi-Tip Dispenser (Thermo Scientific). Plates are centrifuged 1 second at 1000 rpm and incubated 18 to 20 hours at 37° C. in a 5% $CO_2$-controlled incubator. Culture medium is removed from the assay plates by flicking gently on paper towels. 10 μL of assay buffer [1X HBSS (Hyclone, #SH3026801), 20 mM HEPES, pH 7.5 (Hyclone #SH30237.01), 0.1% w/v Casein (CTL Scientific Supply Corp., #440203H), 500 μM IBMX (Sigma-Aldrich #15876)] is added to the wells using the Combi-Tip Dispenser followed by centrifugation for 10 seconds at 1500 rpm. A concentration response curve (20 point) at 2-fold dilutions is prepared in 100% DMSO using acoustic dispensing technology (Labcyte Echo 550). The cells are treated with PYY analogs or human $PYY_{3-36}$ for 45 minutes at 37° C. (final DMSO concentration=1%), then stimulated with 1 μM forskolin (Sigma-Aldrich, #F6886) for 45 minutes at 37° C. The intracellular cAMP is quantified using a CisBio CAMP-G; Dynamic Kit (#62AM9PEB). Briefly, CAMP levels within the cell are detected using the HTRF kit reagents by adding cAMP-d2 conjugate in cell lysis buffer (10 μL) followed by adding the antibody anti-cAMP-$Eu^{3+}$-Cryptate, also in cell lysis buffer (10 μL). The resulting competitive assay is incubated for at least 60 minutes at room temperature, then read on a PerkinElmer Envision™ instrument with excitation at 320 nm and emission at 665 nm and 620 nm. Final assay concentration ranges for peptides tested in response curves are: PYY analogs (0.1 μM to 0.2 μM) and human $PYY_{3-36}$ (10 nM to 0.02 μM). A standard curve of known cAMP concentrations (0.5 μM to 1 μM) is prepared in assay buffer. Wells in the absence of added competitor or with an excess of added human $PYY_{3-36}$ are included on each plate as Maximum Response and Inhibitor Controls, respectively.

Data analysis for hNPY2 receptor CAMP assay—Time-resolved fluorescence emission is used to calculate a fluorescence ratio (665 nM/620 nm), which is inversely proportional to the amount of cAMP present. Signals for PYY analogs and human $PYY_{3-36}$ are converted to nM cAMP per well using a cAMP standard curve plotted as relative response units (emission at 665 nm/620 nm*10,000, y-axis) versus concentration of cAMP (x-axis).

The amount of cAMP generated (nM) in each well is converted to a percent of the maximal response observed with forskolin only as shown in the equation below:

$$\% \text{ Specific Inhibition} = \frac{\text{Peptide} - \text{Inhibitor Control}}{\text{Maximum Response} - \text{Inhibitor Control}},$$

where Inhibitor Control is the CAMP produced in the presence of added excess human $PYY_{3-36}$, Maximum Response is the CAMP produced in the presence of forkolin only, and Peptide is the cAMP produced in the presence of test peptide.

Percent specific inhibition (y-axis) is plotted against the concentration of competitor (x-axis) and analyzed using a four-parameter (curve top, curve bottom, $IC_{50}$, Hill slope) nonlinear regression routine (Genedata Screener, version 13.0.5, Genedata AG, Basal, Switzerland) as defined below:

$$y = \text{bottom} + \frac{\text{top} - \text{bottom}}{1 + \left(\frac{x}{IC50}\right)^{Hill\ Slope}}.$$

The relative $IC_{50}$ value represents the concentration causing 50% inhibition of forskolin-induced cAMP production.

Reported values for $IC_{50}$ are calculated as the geometric mean as shown below: Geometric Mean= $10^{(Arithmetic\ Mean\ of\ Log10\ IC50\ Values)}$.

Standard error of the mean (SEM) is calculated using the delta method as shown below:

$$SEM = \text{Geometric Mean} \times \frac{SD \text{ of log transformed data}}{\text{Square root of } n} \times \ln(10),$$

where SD is the standard deviation, n is the number of independent runs, and In(10) is the natural logarithm of 10.
Results:

TABLE 2

| In Vitro cAMP Activity on the hNPY2 Receptor. | |
|---|---|
| Peptide | hNPY2R $EC_{50}$ (nM) |
| $PYY_{1-36}$ | 0.12 |
| $PYY_{3-36}$ | 0.15 |
| Example 1 | 0.07 |
| Example 2 | 1.23 |
| Example 3 | 0.15 |
| Example 4 | 0.06 |
| Example 5 | 0.55 |
| Ref. 1* | 0.30 |
| Ref. 2* | 0.23 |
| Ref. 3* | 0.32 |

*Known PYY analog for comparison; see, Intl. Patent Application Publication No. WO 2016/198,682, where Ref. 1 corresponds to Compound 4 therein, Ref. 2 corresponds to Compound 21 therein, and Ref. 3 corresponds to Compound 32 therein.

As shown above, results from the CAMP assay demonstrate functional activity of the PYY analogs of Examples 1-5 on the hNPY2 receptor, with Example 2 showing the weakest potency at 12-fold lower potency versus human $PYY_{3-36}$.

(3) In vitro GTPYS activity on the hNPR2 receptor
Purpose:

To assess receptor-mediated activation of G-proteins by the PYY analogs of Examples 1 to 5. Receptor-mediated activation can be measured using the non-hydrolyzable GTP analog, GTPγ[$^{35}$S]. Agonist-mediated stimulation of G-protein-coupled receptors results in the activation of membrane-associated Gαβγ-protein heterotrimeric complexes. This represents a first step in transducing extracellular signals to modify intracellular pathways. Herein, a GTPγ[$^{35}$S] functional assay is used to assess the potency of various PYY analogs at the hNPY2 receptor.

Methods:

PYY analogs, human $PYY_{1-36}$ (SEQ ID NO: 1) and control peptide $PYY_{3-36}$ (SEQ ID NO:2) are synthesized, characterized and stored as described above in the receptor binding assay.

For each test peptide, concentration response curves (CRC) with ⅓ log dilutions (logarithmic concentrations from −6.52 to −12.52) are completed with a Hamilton NIMBUS liquid handler in assay buffer (20 mM HEPES, pH 7.4, 100 mM NaCl, 6 mM $MgCl_2$, 1 mM EDTA) supplemented with 0.2% Bacitracin (U.S. Biologicals #11805) and 0.5% DMSO. Final assay concentrations of Bacitracin and DMSO are 0.05% and 0.125%, respectively. hNPY2R membranes (Multispan #HTS066M) are prepared to a concentration of 7.5 μg/mL in assay buffer supplemented with 20 μM GDP (Sigma #G-7127) and 6 μg/mL Saponin (Sigma #S-4521) and hNPY2R membranes are incubated at room temperature for 20 minutes prior to addition to the assay. $GTP\gamma S[^{35}S]$ (PerkinElmer #NEG030H) is prepared in assay buffer to a concentration of 0.6 nM. WGA SPA beads (PerkinElmer #RPNQ0001) are prepared at concentration of 12 mg/mL in assay buffer. The assay is performed in a 96-well plate (Costar #3604) by first adding 100 μL to the hNPY2R membranes, then 50 μL of CRC solution, then 50 μL of $GTP\gamma S[^{35}S]$ solution for a final volume of 200 μL. The plate is covered and placed on an orbital shaker (175 rpm for 45 minutes) at room temperature. Then, 25 μL of SPA beads are added and plate is re-sealed and vortexed to mix, then placed back on orbital shaker for 3 hours at room temperature. The plate is then centrifuged for 5 minutes at 500 rpm and counted on a PerkinElmer 2450 Microplate counter for 1 minute per well. Basal binding (CPM) is determined in the absence of PYY analog or human $PYY_{3-36}$ and is used to calculate a percent above basal value for each concentration of peptide with the following equation: (PYY analog, or human $PYY_{3-36}$, CPM—Basal CPM)/(Basal CPM)*100. $EC_{50}$ (nM) values is determined by subjecting the logarithm of concentrations and percent of basal values to non-linear regression analysis (log(agonist) vs. response—Variable slope (four parameters)) in GraphPad Prism 7.0 using the equation: $Y=Bottom+(Top-Bottom)/(1+10^{\wedge}((Log\ EC_{50}-X)*HillSlope))$. Geometric mean and standard error of the mean are calculated from $EC_{50}$ (nM) values using the column statistics function in GraphPad Prism 7.0.

Results:

TABLE 3

In Vitro GTPγS Activity on the hNPY2 Receptor.

| Peptide | hNPY2R $EC_{50}$ (nM) |
| --- | --- |
| $PYY_{1-36}$ | 0.42 |
| $PYY_{3-36}$ | 0.43 |
| Example 1 | 0.08 |
| Example 2 | 1.83 |
| Example 3 | 0.06 |
| Example 4 | 0.04 |
| Example 5 | 0.16 |
| Ref. 1* | 0.22 |
| Ref. 2* | 0.13 |
| Ref. 3* | 0.11 |

*Known PYY analog for comparison; see, Intl. Patent Application Publication No. WO 2016/198,682, where Ref. 1 corresponds to Compound 4 therein, Ref. 2 corresponds to Compound 21 therein, and Ref. 3 corresponds to Compound 32 therein.

As shown above, results from the $GTP\gamma[^{35}S]$ functional assay demonstrate activity of the PYY analogs on the hNPY2 receptor, with Example 2 showing the weakest potency at 4-fold lower potency versus human $PYY_{3-36}$.

(4) Pharmacokinetics

Purpose:

To investigate the pharmacokinetic properties of the PYY analogs.

Methods:

LC/MS—Plasma concentrations of various PYY analogs are determined by LC/MS methods. The methods measure the whole compound; peptide plus linked time extension. For the assay, PYY analogs and an internal standard are extracted from mouse, rat or monkey plasma (50 μL) using methanol with 0.1% formic acid. The samples are centrifuged and supernatant is transferred to a Thermo Protein Precipitation Plate. The samples are loaded on a Sep-Pak tC18 SPE μElution Plate that is conditioned with methanol and 0.1% formic acid in water. The SPE columns are washed twice with 0.1% formic acid in water. The compounds are then eluted using Formic Acid/Water/acetonitrile (0.1:15:85), which are then dried and reconstituted prior to injecting an aliquot (10 μL) onto a Thermo Acclaim PepMap 100 $C_{18}$, 300 μm×5 mm trap column and Thermo Easy Spray PepMap $C_{18}$, 75 μm×15 cm column for LC/MS analysis. The column effluent is directed into a Thermo Q-Exactive Plus Mass Spectrometer for detection and quantitation.

Pharmacokinetics of PYY analogs in CD-1 mice—The plasma pharmacokinetics of the PYY analogs are evaluated in male CD-1 mice following a single subcutaneous dose of 200 nmol/kg. Blood samples are collected from 2 animals per time point over 168 hours. Since non-serial sampling is used to evaluate the kinetics of the PYY analogs in mice, the mean concentration versus time data are used to tabulate the pharmacokinetic parameters for the PYY analogs following a single subcutaneous dose of 200 nmol/kg. Plasma concentrations of PYY analogs are detected through 120 hours following a single subcutaneous administration of 200 nmol/kg.

Pharmacokinetics of PYY analogs in SD rats—The plasma pharmacokinetics of the PYY analogs are evaluated in male Sprague Dawley rats following a single subcutaneous dose of 50 nmol/kg. Blood samples are collected from 2 animals per time point over 168 hours. Since serial sampling was used to evaluate the kinetics of the PYY analogs in rats, individual animal concentration versus time data were used to tabulate the pharmacokinetic parameters for the PYY analogs following a single subcutaneous dose of 50 nmol/kg. Plasma concentrations of PYY analogs are detected through 120 hours following a single subcutaneous administration of 50 nmol/kg.

Pharmacokinetics of PYY analogs in cynomolgus monkeys—The plasma pharmacokinetics of the PYY analogs are evaluated in male and female cynomolgus monkeys following a single subcutaneous dose of 50 nmol/kg. Blood samples are collected over 504 hours. Since serial sampling is used to evaluate the kinetics of the PYY analogs in monkeys, individual animal concentration versus time data are used to tabulate the pharmacokinetic parameters for the PYY analogs following a single subcutaneous dose of 50 nmol/kg. Plasma concentrations of PYY analogs are detected through 504 hours following a single subcutaneous administration of 50 nmol/kg.

Results:

TABLE 4

Mean Pharmacokinetic Parameters Following a Single Subcutaneous Dose to Male CD-1 Mice.

| Peptide | Dose (nmol/kg) | $T_{1/2}$ (hr) | $T_{max}$ (hr) | $C_{max}$ (nmol/L) | $AUC_{inf}$ (hr * nmol/L) | CL/F (mL/hr/kg) |
|---|---|---|---|---|---|---|
| Example 1 | 200 | 15 | 6 | 1140 | 29795 | 6.71 |
| Example 2 | 200 | 27 | 12 | 1014 | 56198 | 3.56 |
| Example 3 | 200 | 26 | 12 | 1360 | 52751 | 3.79 |
| Example 4 | 200 | 15 | 12 | 916 | 31257 | 6.40 |

Abbreviations: AUCinf = area under the curve from 0 to infinity; CL/F = clearance divided by bioavailability (F); Cmax = maximum concentration; Tmax = time at maximal concentration; T1/2 = half-life.

TABLE 5

Mean Pharmacokinetic Parameters Following a Single Subcutaneous Dose to Male SD Rats.

| Peptide | Dose (nmol/kg) | $T_{1/2}$ (hr) | $T_{max}$ (hr) | $C_{max}$ (nmol/L) | $AUC_{inf}$ (hr * nmol/L) | CL/F (mL/hr/kg) |
|---|---|---|---|---|---|---|
| Example 1 | 50 | 22 | 12 | 221 | 8621 | 5.83 |
| Example 3 | 50 | 38 | 12 | 399 | 21094 | 2.39 |
| Example 4 | 50 | 19 | 8 | 219 | 8289 | 6.41 |

Abbreviations: $AUC_{inf}$ = area under the curve from 0 to infinity; CL/F = clearance divided by bioavailability (F); $C_{max}$ = maximum concentration; $T_{max}$ = time at maximal concentration; T1/2 = half-life.

TABLE 6

Mean Pharmacokinetic Parameters Following a Single Subcutaneous Dose to Cynomolgus Monkeys.

| Peptide | Dose (nmol/kg) | $T_{1/2}$ (hr) | $T_{max}$ (hr) | $C_{max}$ (nmol/L) | $AUC_{inf}$ (hr * nmol/L) | CL/F (mL/hr/kg) |
|---|---|---|---|---|---|---|
| Example 1 | 50 | 101 | 9 | 500 | 64552 | 0.775 |
| Example 2 | 50 | 131 | 18 | 583 | 123173 | 0.408 |
| Example 3 | 50 | 148 | 9 | 599 | 105839 | 0.509 |

Abbreviations: $AUC_{inf}$ = area under the curve from 0 to infinity; CL/F = clearance divided by bioavailability (F); $C_{max}$ = maximum concentration; $T_{max}$ = time at maximal concentration; T1/2 = half-life.

Results:

These data demonstrate that the above compounds have a pharmacokinetic profile suitable for once weekly administration.

(5) Solubility & Stability

Purpose:

To determine the soluble pH ranges and stability of the PYY analogs

Methods:

Visual solubility range assessment—Lyophilized PYY analog powders are reconstituted in water at 4 mg/mL concentrations, and the pH is adjusted with citric acid/phosphate buffer to pH 4. pH of the system is titrated up with 0.5 N NaCl to pH 8 and then titrated down with 0.5 N HCl to pH 4.

Thermal stability evaluation—PYY analog solutions in 10 mM or 20 mM sodium phosphate, pH 7.0 at 1 mg/mL or 2 mg/mL concentration are prepared and incubated at 4° C. and 40° C. for 4 weeks. The samples at 4-week time point are analyzed by size exclusion chromatography (SEC) and RP-HPLC.

SEC method—Performed using a TOSOH TSKgelG2000SW×1, 7.8 mm ID x 30 cm, 5 μm column, with mobile phase composition of 50 mM sodium phosphate, 300 mM NaCl, pH 7.0 with 20% acetonitrile over 30 minutes with a flow rate of 0.5 mL/min, λ-214 nm.

RP method—Performed using a Cortecs C18, 2.7 μm, 4.6×50 mm column, 20%-45% acetonitrile/water with 0.085% TFA over 10 minutes with a flow rate 1 mL/min, λ-214 nm.

Results:

TABLE 7

Solubility and Thermal Stability of the PYY Analogs.

| | | Thermal Stability (10 or 20 mM Phosphate, pH 7.0) | | | |
|---|---|---|---|---|---|
| | Solubility | RP % Main Peak | | SEC % Main Peak | |
| Peptide | (pH range) | 4° C. | 40° C. | 4° C. | 40° C. |
| Example 1 | >5.7 | 95.8 | 92.9 | 98.9 | 95.7 |
| Example 2 | >5.5 | 99.7 | 99.3 | 99.9 | 99.6 |
| Example 3 | >6.1 | 99.5 | 97.1 | 95.2 | 92.4 |
| Example 4 | >6.8 | 96.8 | 97.5 | 99.6 | 98.7 |
| Example 5 | >5.8 | 96.8 | 95.2 | 99.7 | 97.5 |

As shown above, all the peptides are soluble at pH >7.0. The stability, as assessed by RP and SEC, suggests that these peptides are relative stable under the aggressive thermal stress.

Example 7: In Vivo Effects of PYY (1) In vivo effects on food intake and body weights in normal mice Purpose:

To compare the effect of the PYY analogs of Examples 1 to 5 to reduce body weight and suppress food intake in normal mice after a single injection.

Methods:

Male C57B1/6 mice from Envigo RMS (Indianapolis, IN) are maintained on a chow diet (5008: LabDiet, St. Louis, MO) and single housed in a temperature-controlled facility (74.0•F: 23.3•C) with a normal 12:12-hour light cycle and free access to food and water. At 9-10 weeks of age, non-fasted body weights and initial food weights are recorded, and animals are administered a single subcutaneous injection of vehicle or peptide, followed by daily measurements of body weight and food intake for 3 days post dose. Area under the curve analysis (AUC) is calculated for both body weight and food intake versus vehicle. Example 4 at 30 nmol/kg is used as benchmark of 100% efficacy for body weight and food intake in each run of the assay.

Results:

TABLE 8

Changes in Body Weight and Food Intake for 3 Days in C57/B16 Mice Following a Single Dose of PYY Analog.

| Peptide | Dose (nmol/kg, SC) | Δ Body Weight (%)** | Δ Food Intake (%)** |
|---|---|---|---|
| Example 1 | 30 | 89 | 103 |
| | 100 | 108 | 105 |
| Example 2 | 100 | 71 | 71 |
| | 300 | 117 | 78 |
| Example 3 | 30 | 98 | 93 |
| | 100 | 111 | 100 |
| Example 4 | 3 | 22 | 12 |
| | 10 | 41 | 48 |
| | 30 | 100 | 100 |
| Example 5 | 100 | 70 | 99 |
| | 300 | 129 | 118 |

TABLE 8-continued

Changes in Body Weight and Food Intake for 3 Days in
C57/B16 Mice Following a Single Dose of PYY Analog.

| Peptide | Dose (nmol/kg, SC) | Δ Body Weight (%)** | Δ Food Intake (%)** |
|---|---|---|---|
| Ref. 1* | 100 | 87 | 79 |
|  | 300 | 127 | 104 |
| Ref. 2* | 100 | 62 | 67 |
|  | 300 | 110 | 85 |
| Ref. 3* | 100 | 50 | 78 |
|  | 300 | 104 | 99 |

*Known PYY analog for comparison; see, Inti. Patent Application Publication No. WO 2016/198,682, where Ref. 1 corresponds to Compound 4 therein, Ref. 2 corresponds to Compound 21 therein, and Ref. 3 corresponds to Compound 32 therein.
**Example 4 at 30 nmol/kg (AUCs) set at 100% efficacy As shown above, reductions in both body weight and food intake demonstrate efficacy of the PYY analogs in vivo, where comparisons on doses required for full efficacy demonstrate improvements in efficacy.

(2) In vivo effects on food intake and body weights in diet-induced obese mice
Purpose:
To investigate the effect of daily dosing of the PYY analogs of Examples 1-5 to reduce body weight, either alone or in combination with a GLP-1 receptor agonist, over a two-week period in diet-induced obese (DIO) mice.
Methods:
DIO male C57B1/6 mice (Taconic) at 20 weeks of age are maintained on a 60% fat diet upon arrival (D12492; Research Diets, New Brunswick, NJ). Animals are individually housed in a temperature-controlled facility (74.0•F; 23.3•C) with a 12-hour light/dark cycle (lights on 22:00) and free access to food and water. After a one-week acclimation period of daily vehicle dosing, non-fasted body weights are measured, and animals are randomized by body weight into experimental groups (n=6) and administered daily subcutaneous injections of vehicle, a GLP-1 receptor agonist (GLP-1 RA; SEQ ID NO:15), PYY analogs, or combinations of PYY analogs plus the GLP-1 RA. After 2 weeks of dosing, non-fasted body weights are recorded and changes in average body weight versus vehicle are calculated. To determine additive or synergistic effects of PYY analogs in combination with a GLP-1 RA, efficacy above that of the GLP-1 RA alone (net effect) is calculated.
Results:

TABLE 9

Changes in Body Weight in a 2-Week Study in Diet-
Induced Obese Mice with PYY Analogs Alone or
in Combination with a GLP-1 Receptor Agonist.

| Peptide | Dose (nmol/kg, SC) | Δ Body Weight (%) | |
|---|---|---|---|
| | | PYY Alone | PYY + GLP-1RA* |
| Example 1 | 1 | −4 | −18 |
|  | 3 | −6 | −26 |
|  | 10 | −15 | −31 |
| Example 2 | 3 | ND | −1 |
|  | 10 | ND | −6 |
|  | 30 | 2 | −11 |
| Example 3 | 1 | −3 | −16 |
|  | 3 | −6 | −28 |
|  | 10 | −23 | −30 |
| Example 4 | 0.3 | 0 | −3 |
|  | 1 | −1 | −12 |
|  | 3 | −4 | −17 |
|  | 10 | −12 | −21 |
| Example 5 | 1 | −2 | −2 |
|  | 3 | 0 | −11 |
|  | 10 | −2 | −18 |
|  | 30 | −3 | ND |

*Efficacy above that of a GLP-1 receptor agonist (GLP-1 RA)

As shown above, reductions in body weight with the PYY analogs, both alone and in combination with the GLP-1 RA, demonstrate efficacy of the PYY analogs in vivo, where comparisons are made on the magnitude of weight loss.

(3) In vivo effects on body weight and glucose in diabetic and obese (db/db) mice
Purpose:
To investigate the effect of daily dosing of the PYY analogs of Examples 1 to 5 to reduce body weight and blood glucose levels over a ten-day period in obese and diabetic mice (db/db).
Methods:
Lepr$^{db/db}$ (db/db) male mice from Envigo RMS (Indianapolis, IN) are maintained on a chow-style diet (5008; LabDiet, St. Louis, MO) and housed 5 animals per cage in a temperature-controlled facility (74.0° F.; 23.3•C) with a normal 12:12-hour light cycle and free access to food and water. At 8-9 weeks of age, body weights and blood glucose levels using Accu-Check® Glucometers (Roche Diabetes Care, Inc., Indianapolis, IN) are measured, followed by daily subcutaneous injections of vehicle or peptide. After 10 days of dosing, body weights and blood glucose levels are measured and changes versus vehicle treatment are calculated.
Results:

TABLE 10

Effects on Body Weight and Blood Glucose
in db/db Mice Treated for 10 Days.

| Peptide | Dose (nmol/kg, SC) | Δ Body Weight (%) | Δ Glucose (%) |
|---|---|---|---|
| Example 1 | 1 | −1 | 7 |
|  | 3 | −1 | −10 |
|  | 10 | −10 | −56 |
|  | 30 | −14 | −59 |
| Example 2 | 30 | −5 | −40 |
|  | 100 | −9 | −60 |
|  | 300 | −17 | −67 |
| Example 3 | 1 | 0 | 0 |
|  | 3 | −5 | −7 |
|  | 10 | −9 | −50 |
|  | 30 | −15 | −53 |
| Example 4 | 3 | −2 | −23 |
|  | 10 | −12 | −61 |
|  | 30 | −17 | −62 |
| Example 5 | 10 | −4 | −24 |
|  | 30 | −11 | −59 |
|  | 100 | −17 | −66 |

As shown above, reductions in body weight and blood glucose levels with the PYY analogs demonstrate efficacy of the PYY analogs in vivo, where comparisons are made on the magnitude of weight loss and glucose lowering.

In conclusion, the PYY analogs herein show selectivity toward NPY2R. They also show dose-dependent reductions in body weight, as reflected in normal mice, diet-induced obese mice and db/db mice, as well as dose-dependent improvement in blood glucose in db/db mice, with the PYY analogs of Examples 1, 3 and 4 being the most efficacious, in line with the in vitro profile.

```
                    SEQ ID NO:1 - Human PYY₁₋₃₆
YPIKPEAPGEDASPEELNRYYASLRHYLNLVTRQRY SEQ ID NO:2 - Human PYY₃₋₃₆
IKPEAPGEDASPEELNRYYASLRHYLNLVTRQRY SEQ ID NO:3 - PYY Analog
PKPEX₇PX₉X₁₀DASPEEX₁₇X₁₈RYYX₂₂X₂₃LRHYLNX₃₀LTRQRY SEQ ID NO:4 - PYY Analog
PKPEKPGEDASPEEWQRYYAELRHYLNWLTRQRY SED ID NOR:5 - PPYY Analog
PKPEKPGEDASPEEWQRYYAELRHYLNELTRQRY SEQ ID NO:6 - PYY Analog
PKPEKPEEDASPEEWQRYYIELRHYLNWLTRQRY SEQ ID NO:7 = PYY Analog
PKPEKPGKDASPEEWNRYYADLRHYLNWLTRQRY SEQ ID NO:8 - PYY Analog
PKPEKPGEDASPEELQRYYASLRHYLNWLTRQRY
```

SEQ ID NO:9—PYY Analog

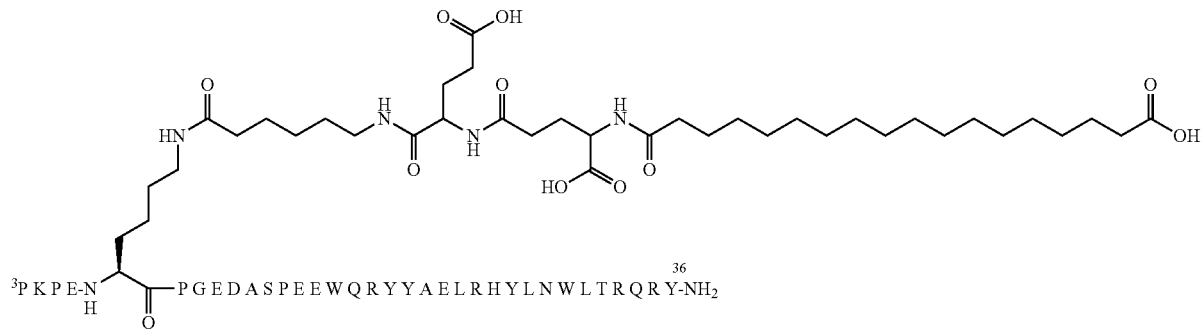

SEQ ID NO:10—PYY Analog

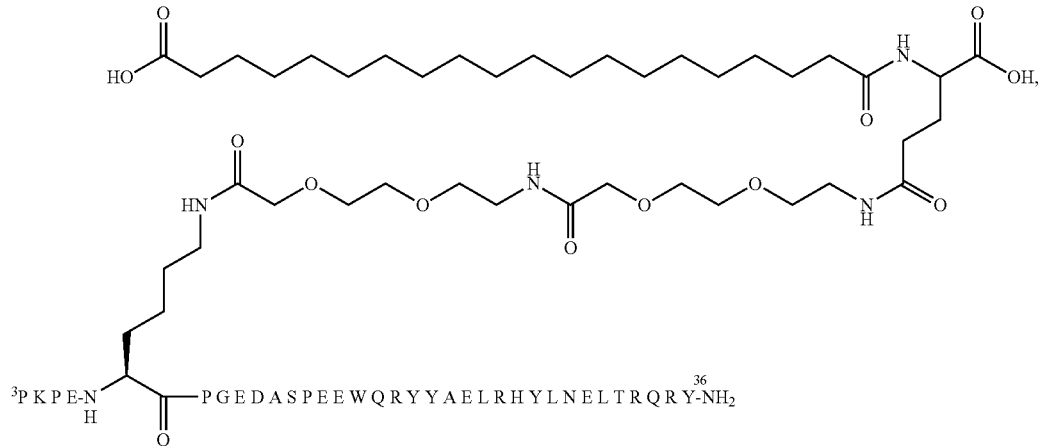

SEQ ID NO:11—PYY Analog

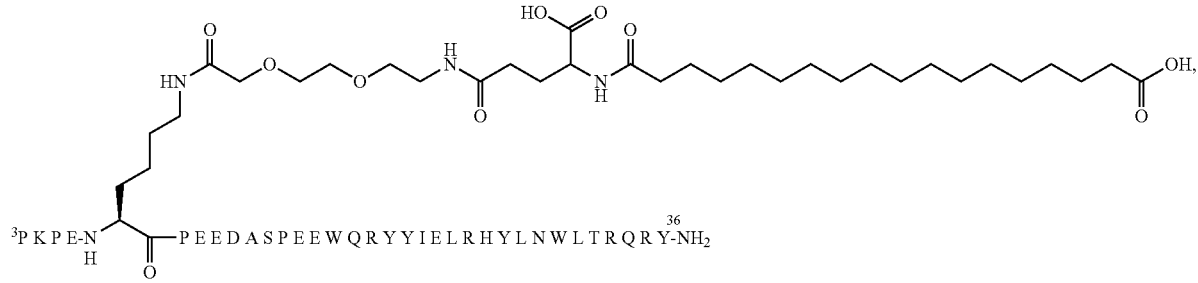

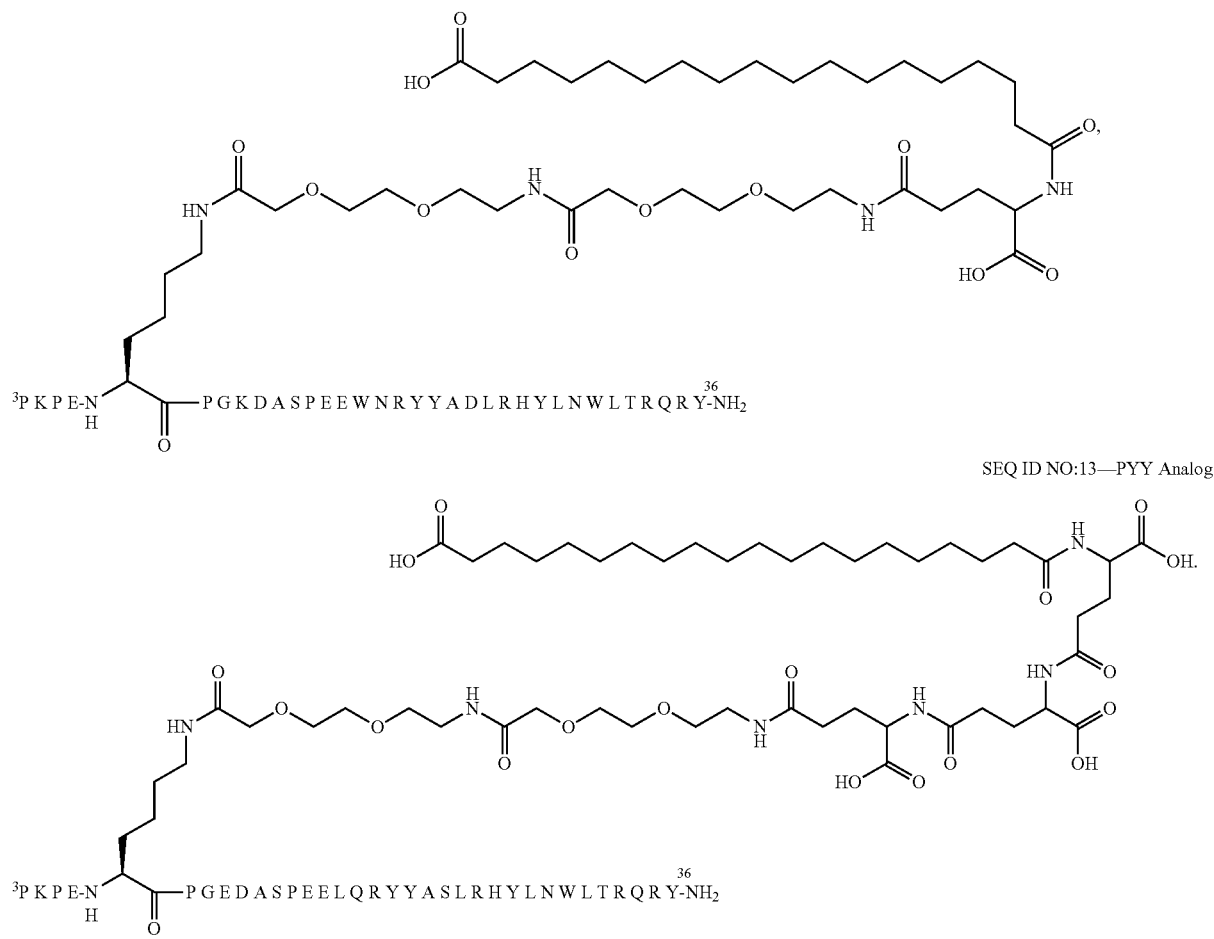

SEQ ID NO:12—PYY Analog

SEQ ID NO:13—PYY Analog

SEQ ID NO:14 - PP$_{1-36}$
APLEPVYPGDNATPEQMAQYAADLRRYINMLTRPRY

SEQ ID NO:15 - GLP-1 RA
HGEGTFTSDVSSYLEEQAAKEFIAWLVKGRGGGGSGGGGSGGGGSESKY
GPPCPPCPAPEAAGGPSVFLFPPKPKDTLMISRTPEVTCVVVDVSQEDPE
VQFNWYVDGVEVHNAKTKPREEQFNSTYRVVSVLTVLHQDWLNGKEYKCK
VSNKGLPSSIEKTISKAKGQPREPQVYTLPPSQEEMTKNQVSLTCLVKGF
YPSDIAVEWESNGQPENNYKTTPPVLDSDGSFFLYSRLTVDKSRWQEGNV
FSCSVMHEALHNHYTQKSLSLSLG

The invention claimed is:

1. A Peptide Tyrosine-Tyrosine (PYY) analog comprising an amino acid sequence of:

PKPEX7PX9X10DASPEEX17X18RYYX22X23LRHYLNX30LTRQRY, (Formula I)

wherein $X_7$ is any amino acid with a functional group available for conjugation and the functional group is conjugated to a $C_{16}$-$C_{22}$ fatty acid,
wherein $X_9$ is E or G,
wherein $X_{10}$ is E or K,
wherein $X_{17}$ is L or W,
wherein $X_{18}$ is N or Q,
wherein $X_{22}$ is A or I,
wherein $X_{23}$ is E, D or S,
wherein $X_{30}$ is E or W (SEQ ID NO:3), and
wherein a C-terminal amino acid is optionally amidated.

2. The PYY analog of claim 1, wherein the amino acid sequence is selected from the group consisting of:

PKPEKPGEDASPEEWQRYYAELRHYLNWLTRQRY; (SEQ ID NO: 4)

PKPEKPGEDASPEEWQRYYAELRHYLNELTRQRY; (SEQ ID NO: 5)

PKPEKPEEDASPEEWQRYYIELRHYLNWLTRQRY; (SEQ ID NO: 6)

PKPEKPGKDASPEEWNRYYADLRHYLNWLTRQRY; and (SEQ ID NO: 7)

PKPEKPGEDASPEELQRYYASLRHYLNWLTRQRY. (SEQ ID NO: 8)

3. The PYY analog of claim 1, wherein the $C_{16}$-$C_{22}$ fatty acid is selected from the group consisting of a hexadecanoic acid, a hexadecanedioic acid, a heptadecanoic acid, a heptadecanedioic acid, a stearic acid, an octadecanedioic acid, a nonadecylic acid, a nonadecanedioic acid, an eicosanoic acid, an eicosanedioic acid, a heneicosanoic acid, a heneicosanedioic acid, a docosanoic acid, a docosanedioic acid, and branched and substituted derivatives thereof.

4. The PYY analog of claim 1, wherein the $C_{16}$-$C_{22}$ fatty acid is a $C_{18}$-$C_{20}$ fatty acid.

5. The PYY analog of claim 4, wherein the $C_{18}$-$C_{20}$ fatty acid is a straight-chain fatty acid having a formula of $CO$-$(CH_2)_x$-$CO_2H$, and wherein x is 18 or 20.

6. The PYY analog of claim 5, wherein the $C_{18}$-$C_{20}$ fatty acid is selected from the group consisting of palmitic acid, stearic acid, arachidic acid and eicosanoic acid.

7. The PYY analog of claim 1, wherein the amino acid sequence is:

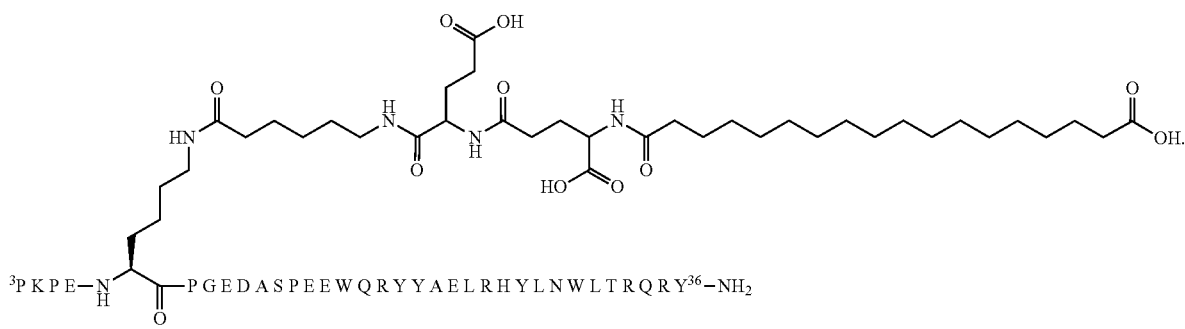

(SEQ ID NO:9)

8. The PYY analog of claim 1, wherein the amino acid sequence is:
(SEQ ID NO:10)
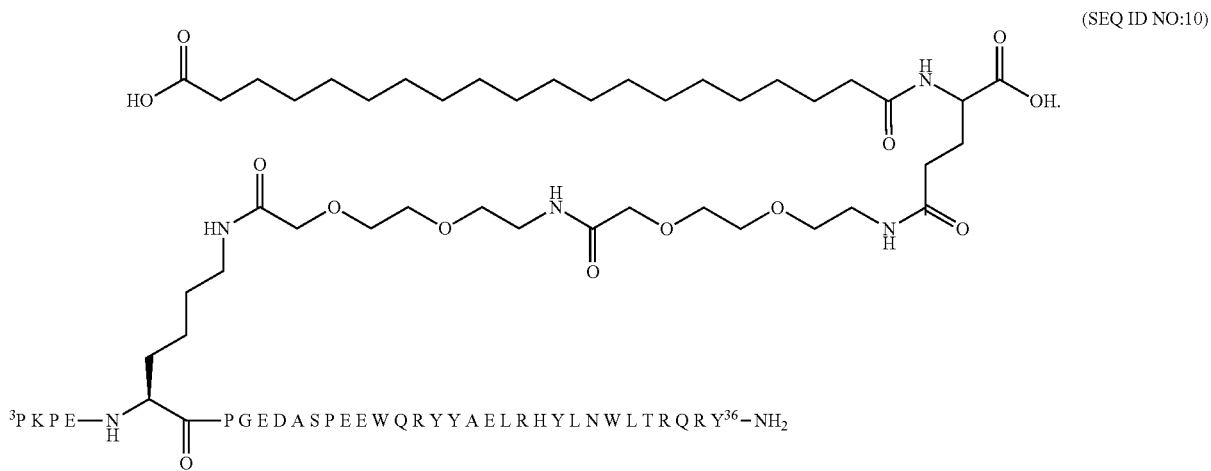
9. The PYY analog of claim 1, wherein the amino acid sequence is:
(SEQ ID NO:11)
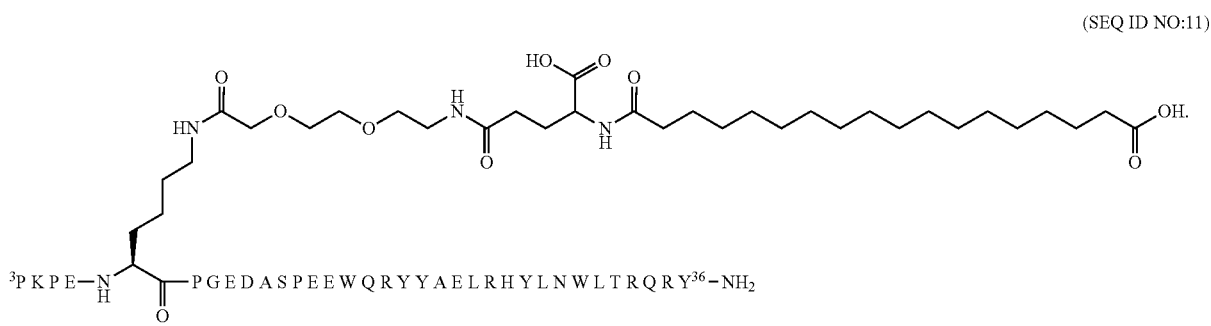
10. The PYY analog of claim 1, wherein the amino acid sequence is:
(SEQ ID NO:12)
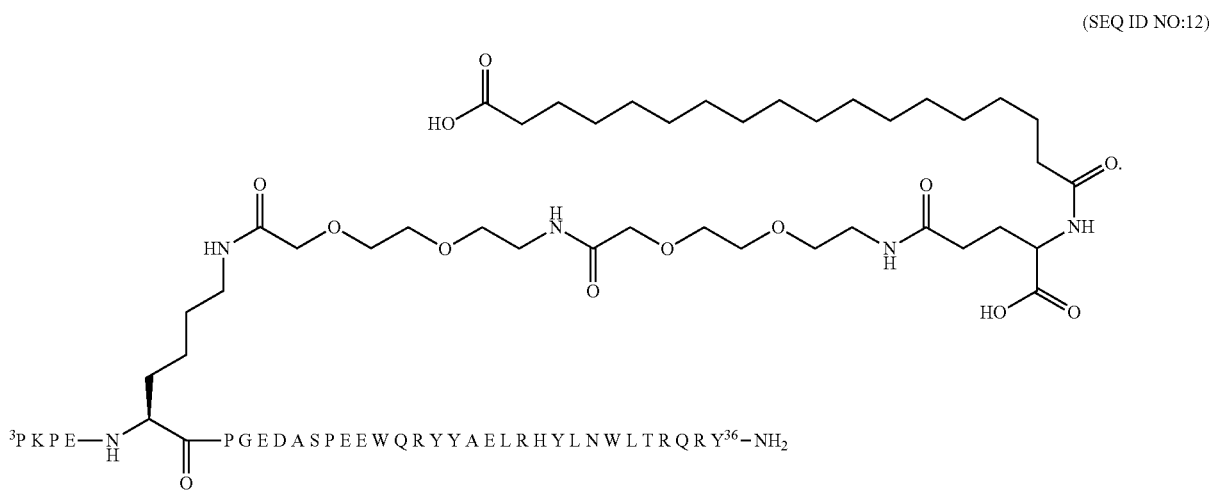

11. The PYY analog of claim 1, wherein the amino acid sequence is:
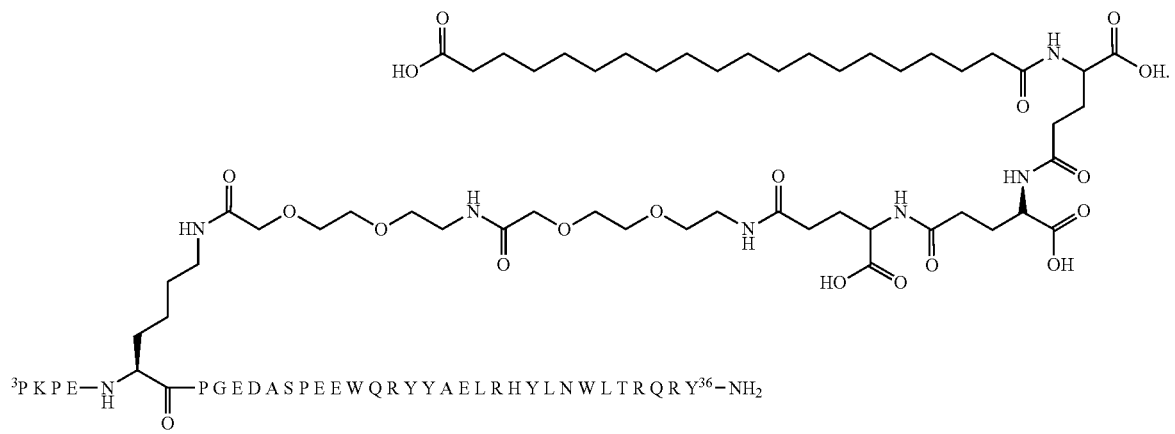
(SEQ ID NO:13)
12. A pharmaceutical composition comprising:
at least one Peptide Tyrosine-Tyrosine (PYY) analog of claim 1 or a salt thereof; and one or more pharmaceutically acceptable carriers, diluents and excipients.
* * * * *

UNITED STATES PATENT AND TRADEMARK OFFICE
CERTIFICATE OF CORRECTION

| | | |
|---|---|---|
| PATENT NO. | : 12,269,857 B2 | Page 1 of 1 |
| APPLICATION NO. | : 18/484451 | |
| DATED | : April 8, 2025 | |
| INVENTOR(S) | : Daniel Anthony Briere et al. | |

It is certified that error appears in the above-identified patent and that said Letters Patent is hereby corrected as shown below:

In the Claims

Column 45, Line 23, In Claim 1, delete "PKPEX7PX9X10DASPEEX17X18RYYX22X23LRHYLNX30LTRQRY," and insert -- $PKPEX_7PX_9X_{10}DASPEEX_{17}X_{18}RYYX_{22}X_{23}LRHYLNX_{30}LTRQRY$, --.

Column 45, Line 24, In Claim 1, delete "$X_7$is" and insert -- $X_7$ is --.

Column 45, Line 29, In Claim 1, delete "$X_{17}$is" and insert -- $X_{17}$ is --.

Signed and Sealed this
Twenty-first Day of October, 2025

John A. Squires
*Director of the United States Patent and Trademark Office*